(12) United States Patent
Griffith

(10) Patent No.: US 8,100,922 B2
(45) Date of Patent: Jan. 24, 2012

(54) CURVED NEEDLE SUTURING TOOL

(75) Inventor: David B. Griffith, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1275 days.

(21) Appl. No.: 11/796,357

(22) Filed: Apr. 27, 2007

(65) Prior Publication Data

US 2008/0269783 A1  Oct. 30, 2008

(51) Int. Cl.
*A61B 17/04* (2006.01)
(52) U.S. Cl. ............................................... 606/144
(58) Field of Classification Search ............ 606/139, 606/144, 145, 147, 148, 222–227
See application file for complete search history.

(56) References Cited

U.S. PATENT DOCUMENTS

| | | |
|---|---|---|
| 645,576 A | 3/1900 | Telsa |
| 649,621 A | 5/1900 | Tesla |
| 787,412 A | 4/1905 | Tesla |
| 1,127,948 A | 2/1915 | Wappler |
| 1,482,653 A | 2/1924 | Lilly |
| 1,625,602 A | 4/1927 | Gould et al. |
| 2,028,635 A | 1/1936 | Wappler |
| 2,113,246 A | 4/1938 | Wappler |
| 2,155,365 A | 4/1939 | Rankin |
| 2,191,858 A | 2/1940 | Moore |
| 2,196,620 A | 4/1940 | Attarian |
| 2,388,137 A | 10/1945 | Graumlich |
| 2,493,108 A | 1/1950 | Casey, Jr. |
| 2,504,152 A | 4/1950 | Riker et al. |
| 2,952,206 A | 9/1960 | Becksted |
| 3,069,195 A | 12/1962 | Buck |
| 3,170,471 A | 2/1965 | Schnitzer |
| 3,435,824 A | 4/1969 | Gamponia |
| 3,470,876 A | 10/1969 | Barchilon |
| 3,669,487 A | 6/1972 | Roberts et al. |
| 3,746,881 A | 7/1973 | Fitch et al. |
| 3,799,672 A | 3/1974 | Vurek |

(Continued)

FOREIGN PATENT DOCUMENTS

AU 666310 B2 2/1996

(Continued)

OTHER PUBLICATIONS

International Search Report for PCT/US2008/061269, Sep. 10, 2008 (7 pages).

(Continued)

*Primary Examiner* — Darwin Erezo

(57) ABSTRACT

A needle delivery device is described and includes generally, a needle made of a shape memory alloy pre-formed in an unconstrained configuration, such as, for example, an arc or a curved needle. The needle delivery device also includes a needle delivery guide, a suturing guide and a positioning member. The needle has an eye at its leading tip for holding suture material. The needle delivery guide has a needle channel for passage of the needle therethrough. The needle channel is configured to hold the needle in a constrained configuration, for example, in substantial alignment with the longitudinal axis of the needle channel. The suturing guide is pivotally connected to the delivery guide. The positioning member moves the suturing guide between an extended position and a collapsed position, wherein, in the extended position, the suturing guide is configured to stabilize the tissue and guide the needle in its unconstrained configuration and to enable access by, for example, a grasper or other tool, to the suture material.

11 Claims, 7 Drawing Sheets

U.S. PATENT DOCUMENTS

| | | |
|---|---|---|
| 3,946,740 A | 3/1976 | Bassett |
| 3,994,301 A | 11/1976 | Agris |
| 4,011,872 A | 3/1977 | Komiya |
| 4,012,812 A | 3/1977 | Black |
| 4,164,225 A * | 8/1979 | Johnson et al. ............... 606/145 |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,278,077 A | 7/1981 | Mizumoto |
| 4,285,344 A | 8/1981 | Marshall |
| 4,311,143 A | 1/1982 | Komiya |
| 4,396,021 A | 8/1983 | Baumgartner |
| 4,452,246 A | 6/1984 | Bader et al. |
| 4,461,281 A | 7/1984 | Carson |
| 4,491,132 A | 1/1985 | Aikins |
| 4,527,331 A | 7/1985 | Lasner et al. |
| 4,527,564 A * | 7/1985 | Eguchi et al. .................. 606/223 |
| 4,538,594 A | 9/1985 | Boebel et al. |
| D281,104 S | 10/1985 | Davison |
| 4,580,551 A | 4/1986 | Siegmund et al. |
| 4,646,722 A | 3/1987 | Silverstein et al. |
| 4,653,476 A | 3/1987 | Bonnet |
| 4,669,470 A | 6/1987 | Brandfield |
| 4,671,477 A | 6/1987 | Cullen |
| 4,685,447 A | 8/1987 | Iversen et al. |
| 4,711,240 A | 12/1987 | Goldwasser et al. |
| 4,712,545 A | 12/1987 | Honkanen |
| 4,721,116 A | 1/1988 | Schintgen et al. |
| 4,733,662 A | 3/1988 | DeSatnick et al. |
| D295,894 S | 5/1988 | Sharkany et al. |
| 4,763,669 A | 8/1988 | Jaeger |
| 4,770,188 A | 9/1988 | Chikama |
| 4,815,450 A | 3/1989 | Patel |
| 4,823,794 A | 4/1989 | Pierce |
| 4,829,999 A | 5/1989 | Auth |
| 4,873,979 A | 10/1989 | Hanna |
| 4,880,015 A | 11/1989 | Nierman |
| 4,911,148 A | 3/1990 | Sosnowski et al. |
| 4,926,860 A | 5/1990 | Stice et al. |
| 4,938,214 A | 7/1990 | Specht et al. |
| 4,950,273 A | 8/1990 | Briggs |
| 4,950,285 A | 8/1990 | Wilk |
| 4,984,581 A | 1/1991 | Stice |
| 5,007,917 A | 4/1991 | Evans |
| 5,010,876 A | 4/1991 | Henley et al. |
| 5,020,514 A | 6/1991 | Heckele |
| 5,020,535 A | 6/1991 | Parker et al. |
| 5,025,778 A | 6/1991 | Silverstein et al. |
| 5,033,169 A | 7/1991 | Bindon |
| 5,037,433 A * | 8/1991 | Wilk et al. .................... 606/139 |
| 5,041,129 A | 8/1991 | Hayhurst et al. |
| 5,046,513 A | 9/1991 | Gatturna et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,123,913 A | 6/1992 | Wilk et al. |
| 5,123,914 A | 6/1992 | Cope |
| 5,133,727 A | 7/1992 | Bales et al. |
| 5,174,300 A | 12/1992 | Bales et al. |
| 5,176,126 A | 1/1993 | Chikama |
| 5,190,050 A | 3/1993 | Nitzsche |
| 5,190,555 A | 3/1993 | Wetter et al. |
| 5,192,284 A | 3/1993 | Pleatman |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A * | 6/1993 | Bendel et al. ................. 606/222 |
| 5,222,362 A | 6/1993 | Maus et al. |
| 5,222,965 A | 6/1993 | Haughton |
| 5,234,453 A | 8/1993 | Smith et al. |
| 5,235,964 A | 8/1993 | Abenaim |
| 5,242,456 A | 9/1993 | Nash et al. |
| 5,246,424 A | 9/1993 | Wilk |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,284,128 A | 2/1994 | Hart |
| 5,284,162 A | 2/1994 | Wilk |
| 5,287,845 A | 2/1994 | Faul et al. |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,301,061 A | 4/1994 | Nakada et al. |
| 5,312,351 A | 5/1994 | Gerrone |
| 5,312,416 A | 5/1994 | Spaeth et al. |
| 5,312,423 A | 5/1994 | Rosenbluth et al. |
| 5,320,636 A | 6/1994 | Slater |
| 5,325,845 A | 7/1994 | Adair |
| 5,330,471 A | 7/1994 | Eggers |
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,198 A | 8/1994 | Hart et al. |
| 5,344,428 A | 9/1994 | Griffiths |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,408 A | 10/1994 | Rydell |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A | 12/1994 | Graber et al. |
| 5,374,273 A | 12/1994 | Nakao et al. |
| 5,374,275 A | 12/1994 | Bradley et al. |
| 5,374,277 A | 12/1994 | Hassler |
| 5,377,695 A | 1/1995 | An Haack |
| 5,383,877 A | 1/1995 | Clarke |
| 5,383,888 A | 1/1995 | Zvenyatsky et al. |
| 5,391,174 A | 2/1995 | Weston |
| 5,392,789 A | 2/1995 | Slater et al. |
| 5,395,386 A | 3/1995 | Slater |
| 5,401,248 A | 3/1995 | Bencini |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,433,721 A | 7/1995 | Hooven et al. |
| 5,439,471 A | 8/1995 | Kerr |
| 5,439,478 A | 8/1995 | Palmer |
| 5,441,059 A | 8/1995 | Dannan |
| 5,441,499 A | 8/1995 | Fritzsch |
| 5,449,021 A | 9/1995 | Chikama |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,460,629 A | 10/1995 | Shlain et al. |
| 5,462,561 A | 10/1995 | Voda |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,478,347 A | 12/1995 | Aranyi |
| 5,480,404 A | 1/1996 | Kammerer et al. |
| 5,482,054 A | 1/1996 | Slater et al. |
| 5,484,451 A | 1/1996 | Akopov et al. |
| 5,489,256 A | 2/1996 | Adair |

| | | | | | |
|---|---|---|---|---|---|
| 5,496,347 A | 3/1996 | Hashiguchi et al. | 5,792,165 A | 8/1998 | Klieman et al. |
| 5,499,990 A | 3/1996 | Schülken et al. | 5,797,835 A | 8/1998 | Green |
| 5,499,992 A | 3/1996 | Meade et al. | 5,797,928 A | 8/1998 | Kogasaka |
| 5,501,692 A | 3/1996 | Riza | 5,797,939 A | 8/1998 | Yoon |
| 5,503,616 A | 4/1996 | Jones | 5,797,941 A | 8/1998 | Schulze et al. |
| 5,505,686 A | 4/1996 | Willis et al. | 5,803,903 A | 9/1998 | Athas et al. |
| 5,507,755 A | 4/1996 | Gresl et al. | 5,808,665 A | 9/1998 | Green |
| 5,511,564 A | 4/1996 | Wilk | 5,810,806 A | 9/1998 | Ritchart et al. |
| 5,514,157 A | 5/1996 | Nicholas et al. | 5,810,849 A | 9/1998 | Kontos |
| 5,522,829 A | 6/1996 | Michalos | 5,810,865 A | 9/1998 | Koscher et al. |
| 5,522,830 A | 6/1996 | Aranyi | 5,810,876 A | 9/1998 | Kelleher |
| 5,527,321 A | 6/1996 | Hinchliffe | 5,810,877 A | 9/1998 | Roth et al. |
| 5,540,648 A | 7/1996 | Yoon | 5,813,976 A | 9/1998 | Filipi et al. |
| 5,554,151 A | 9/1996 | Hinchliffe | 5,814,058 A | 9/1998 | Carlson et al. |
| 5,558,133 A | 9/1996 | Bortoli et al. | 5,817,061 A | 10/1998 | Goodwin et al. |
| 5,562,693 A | 10/1996 | Devlin et al. | 5,817,107 A | 10/1998 | Schaller |
| 5,569,243 A | 10/1996 | Kortenbach et al. | 5,817,119 A | 10/1998 | Klieman et al. |
| 5,569,298 A | 10/1996 | Schnell | 5,819,736 A | 10/1998 | Avny et al. |
| 5,573,540 A | 11/1996 | Yoon | 5,827,281 A | 10/1998 | Levin |
| 5,578,030 A | 11/1996 | Levin | 5,827,299 A | 10/1998 | Thomason et al. |
| 5,582,611 A | 12/1996 | Tsuruta et al. | 5,830,231 A | 11/1998 | Geiges, Jr. |
| 5,582,617 A | 12/1996 | Klieman et al. | 5,833,700 A | 11/1998 | Fogelberg et al. |
| 5,584,845 A | 12/1996 | Hart | 5,833,703 A | 11/1998 | Manushakian |
| 5,591,179 A | 1/1997 | Edelstein | 5,843,017 A | 12/1998 | Yoon |
| 5,593,420 A | 1/1997 | Eubanks, Jr et al. | 5,849,022 A | 12/1998 | Sakashita et al. |
| 5,595,562 A | 1/1997 | Grier | 5,853,374 A | 12/1998 | Hart et al. |
| 5,597,378 A | 1/1997 | Jervis | 5,855,585 A | 1/1999 | Kontos |
| 5,601,573 A | 2/1997 | Fogelberg et al. | 5,860,913 A | 1/1999 | Yamaya et al. |
| 5,601,588 A | 2/1997 | Tonomura et al. | 5,860,995 A | 1/1999 | Berkelaar |
| 5,604,531 A | 2/1997 | Iddan et al. | 5,868,762 A | 2/1999 | Cragg et al. |
| 5,607,389 A | 3/1997 | Edwards et al. | 5,876,411 A | 3/1999 | Kontos |
| 5,607,450 A | 3/1997 | Zvenyatsky et al. | 5,882,331 A | 3/1999 | Sasaki |
| 5,613,975 A | 3/1997 | Christy | 5,882,344 A | 3/1999 | Stouder, Jr. |
| 5,618,303 A | 4/1997 | Marlow et al. | 5,893,846 A | 4/1999 | Bales et al. |
| 5,620,415 A | 4/1997 | Lucey et al. | 5,893,874 A | 4/1999 | Bourque et al. |
| 5,624,399 A | 4/1997 | Ackerman | 5,893,875 A | 4/1999 | O'Connor et al. |
| 5,624,431 A | 4/1997 | Gerry et al. | 5,899,919 A | 5/1999 | Eubanks, Jr. et al. |
| 5,628,732 A | 5/1997 | Antoon, Jr. et al. | 5,904,702 A | 5/1999 | Ek et al. |
| 5,630,782 A | 5/1997 | Adair | 5,908,420 A | 6/1999 | Parins et al. |
| 5,643,283 A | 7/1997 | Younker | 5,916,147 A | 6/1999 | Boury |
| 5,643,292 A | 7/1997 | Hart | 5,921,993 A | 7/1999 | Yoon |
| 5,643,294 A | 7/1997 | Tovey et al. | 5,921,997 A | 7/1999 | Fogelberg et al. |
| 5,645,083 A | 7/1997 | Essig et al. | 5,922,008 A | 7/1999 | Gimpelson |
| 5,649,372 A | 7/1997 | Souza | 5,925,052 A | 7/1999 | Simmons |
| 5,653,677 A | 8/1997 | Okada et al. | 5,928,255 A | 7/1999 | Meade et al. |
| 5,653,722 A | 8/1997 | Kieturakis | 5,928,266 A | 7/1999 | Kontos |
| 5,662,663 A | 9/1997 | Shallman | 5,936,536 A | 8/1999 | Morris |
| 5,669,875 A | 9/1997 | van Eerdenburg | 5,944,718 A | 8/1999 | Austin et al. |
| 5,681,324 A | 10/1997 | Kammerer et al. | 5,951,549 A | 9/1999 | Richardson et al. |
| 5,681,330 A | 10/1997 | Hughett et al. | 5,954,720 A | 9/1999 | Wilson et al. |
| 5,685,820 A | 11/1997 | Riek et al. | 5,954,731 A | 9/1999 | Yoon |
| 5,690,656 A | 11/1997 | Cope et al. | 5,957,943 A | 9/1999 | Vaitekunas |
| 5,690,660 A | 11/1997 | Kauker et al. | 5,957,953 A | 9/1999 | DiPoto et al. |
| 5,695,448 A | 12/1997 | Kimura et al. | 5,971,995 A | 10/1999 | Rousseau |
| 5,695,505 A | 12/1997 | Yoon | 5,976,074 A | 11/1999 | Moriyama |
| 5,695,511 A | 12/1997 | Cano et al. | 5,976,075 A | 11/1999 | Beane et al. |
| 5,700,275 A | 12/1997 | Bell et al. | 5,976,130 A | 11/1999 | McBrayer et al. |
| 5,704,892 A | 1/1998 | Adair | 5,976,131 A | 11/1999 | Guglielmi et al. |
| 5,709,708 A | 1/1998 | Thal | 5,980,539 A | 11/1999 | Kontos |
| 5,716,326 A | 2/1998 | Dannan | 5,980,556 A | 11/1999 | Giordano et al. |
| 5,730,740 A | 3/1998 | Wales et al. | 5,984,938 A | 11/1999 | Yoon |
| 5,741,278 A | 4/1998 | Stevens | 5,989,182 A | 11/1999 | Hori et al. |
| 5,741,285 A | 4/1998 | McBrayer et al. | 5,993,447 A | 11/1999 | Blewett et al. |
| 5,746,759 A | 5/1998 | Meade et al. | 5,997,555 A | 12/1999 | Kontos |
| 5,749,881 A | 5/1998 | Sackier et al. | 6,001,120 A | 12/1999 | Levin |
| 5,749,889 A | 5/1998 | Bacich et al. | 6,004,330 A | 12/1999 | Middleman et al. |
| 5,752,951 A | 5/1998 | Yanik | 6,007,566 A | 12/1999 | Wenstrom, Jr. |
| 5,766,167 A | 6/1998 | Eggers et al. | 6,010,515 A | 1/2000 | Swain et al. |
| 5,766,170 A | 6/1998 | Eggers | 6,019,770 A | 2/2000 | Christoudias |
| 5,766,205 A | 6/1998 | Zvenyatsky et al. | 6,024,708 A | 2/2000 | Bales et al. |
| 5,769,849 A | 6/1998 | Eggers | 6,024,747 A | 2/2000 | Kontos |
| 5,779,701 A | 7/1998 | McBrayer et al. | 6,027,522 A | 2/2000 | Palmer |
| 5,779,716 A | 7/1998 | Cano et al. | 6,030,365 A | 2/2000 | Laufer |
| 5,779,727 A | 7/1998 | Orejola | 6,033,399 A | 3/2000 | Gines |
| 5,782,859 A | 7/1998 | Nicholas et al. | 6,053,927 A | 4/2000 | Hamas |
| 5,782,866 A | 7/1998 | Wenstrom, Jr. | 6,066,160 A | 5/2000 | Colvin et al. |
| 5,791,022 A | 8/1998 | Bohman | 6,068,603 A | 5/2000 | Suzuki |
| 5,792,113 A | 8/1998 | Kramer et al. | 6,068,629 A | 5/2000 | Haissaguerre et al. |
| 5,792,153 A | 8/1998 | Swain et al. | 6,071,233 A | 6/2000 | Ishikawa et al. |

| | | | | | | |
|---|---|---|---|---|---|---|
| 6,074,408 A | 6/2000 | Freeman | | 6,585,642 B2 | 7/2003 | Christopher |
| 6,086,530 A | 7/2000 | Mack | | 6,592,559 B1 | 7/2003 | Pakter et al. |
| 6,090,108 A | 7/2000 | McBrayer et al. | | 6,592,603 B2 | 7/2003 | Lasner |
| 6,096,046 A | 8/2000 | Weiss | | 6,602,262 B2 | 8/2003 | Griego et al. |
| 6,110,154 A | 8/2000 | Shimomura et al. | | 6,605,105 B1 | 8/2003 | Cuschieri et al. |
| 6,110,183 A | 8/2000 | Cope | | 6,610,072 B1 | 8/2003 | Christy et al. |
| 6,113,593 A | 9/2000 | Tu et al. | | 6,610,074 B2 | 8/2003 | Santilli |
| 6,117,144 A | 9/2000 | Nobles et al. | | 6,626,919 B1 | 9/2003 | Swanstrom |
| 6,117,158 A | 9/2000 | Measamer et al. | | 6,632,229 B1 | 10/2003 | Yamanouchi |
| 6,139,555 A | 10/2000 | Hart et al. | | 6,638,286 B1 | 10/2003 | Burbank et al. |
| 6,146,391 A | 11/2000 | Cigaina | | 6,652,521 B2 | 11/2003 | Schulze |
| 6,149,653 A | 11/2000 | Deslauriers | | 6,652,551 B1 | 11/2003 | Heiss |
| 6,149,662 A | 11/2000 | Pugliesi et al. | | 6,656,194 B1 | 12/2003 | Gannoe et al. |
| 6,159,200 A | 12/2000 | Verdura et al. | | 6,663,641 B1 | 12/2003 | Kovac et al. |
| 6,165,184 A | 12/2000 | Verdura et al. | | 6,666,854 B1 | 12/2003 | Lange |
| 6,168,570 B1 | 1/2001 | Ferrera | | 6,672,338 B1 | 1/2004 | Esashi et al. |
| 6,168,605 B1 | 1/2001 | Measamer et al. | | 6,673,087 B1 | 1/2004 | Chang et al. |
| 6,170,130 B1 | 1/2001 | Hamilton et al. | | 6,685,628 B2 | 2/2004 | Vu |
| 6,179,776 B1 | 1/2001 | Adams et al. | | 6,685,724 B1 | 2/2004 | Haluck |
| 6,179,837 B1 | 1/2001 | Hooven | | 6,692,445 B2 | 2/2004 | Roberts et al. |
| 6,190,353 B1 | 2/2001 | Makower et al. | | 6,692,462 B2 | 2/2004 | Mackenzie et al. |
| 6,190,384 B1 | 2/2001 | Ouchi | | 6,699,180 B2 | 3/2004 | Kobayashi |
| 6,190,399 B1 | 2/2001 | Palmer et al. | | 6,699,256 B1 | 3/2004 | Logan et al. |
| 6,203,533 B1 | 3/2001 | Ouchi | | 6,699,263 B2 | 3/2004 | Cope |
| 6,206,872 B1 | 3/2001 | Lafond et al. | | 6,708,066 B2 | 3/2004 | Herbst et al. |
| 6,206,877 B1 | 3/2001 | Kese et al. | | 6,716,226 B2 | 4/2004 | Sixto, Jr. et al. |
| 6,214,007 B1 | 4/2001 | Anderson | | 6,740,030 B2 | 5/2004 | Martone et al. |
| 6,228,096 B1 | 5/2001 | Marchand | | 6,743,240 B2 | 6/2004 | Smith et al. |
| 6,245,079 B1 | 6/2001 | Nobles et al. | | 6,749,560 B1 | 6/2004 | Konstorum et al. |
| 6,258,064 B1 | 7/2001 | Smith et al. | | 6,749,609 B1 | 6/2004 | Lunsford et al. |
| 6,261,242 B1 | 7/2001 | Roberts et al. | | 6,752,768 B2 | 6/2004 | Burdorff et al. |
| 6,264,664 B1 | 7/2001 | Avellanet | | 6,752,811 B2 | 6/2004 | Chu et al. |
| 6,270,497 B1 | 8/2001 | Sekino et al. | | 6,752,822 B2 | 6/2004 | Jespersen |
| 6,270,505 B1 | 8/2001 | Yoshida et al. | | 6,761,685 B2 | 7/2004 | Adams et al. |
| 6,277,136 B1 | 8/2001 | Bonutti | | 6,761,718 B2 | 7/2004 | Madsen |
| 6,283,963 B1 | 9/2001 | Regula | | 6,773,434 B2 | 8/2004 | Ciarrocca |
| 6,293,909 B1 | 9/2001 | Chu et al. | | 6,780,151 B2 | 8/2004 | Grabover et al. |
| 6,293,952 B1 | 9/2001 | Brosens et al. | | 6,780,352 B2 | 8/2004 | Jacobson |
| 6,296,630 B1 | 10/2001 | Altman et al. | | 6,783,491 B2 | 8/2004 | Saadat et al. |
| 6,322,578 B1 | 11/2001 | Houle et al. | | 6,786,864 B2 | 9/2004 | Matsuura et al. |
| 6,326,177 B1 | 12/2001 | Schoenbach et al. | | 6,790,173 B2 | 9/2004 | Saadat et al. |
| 6,328,730 B1 | 12/2001 | Harkrider, Jr. | | 6,795,728 B2 | 9/2004 | Chornenky et al. |
| 6,350,267 B1 | 2/2002 | Stefanchik | | 6,800,056 B2 | 10/2004 | Tartaglia et al. |
| 6,352,503 B1 | 3/2002 | Matsui et al. | | 6,808,491 B2 | 10/2004 | Kortenbach et al. |
| 6,352,543 B1 | 3/2002 | Cole | | 6,824,548 B2 | 11/2004 | Smith et al. |
| 6,355,035 B1 | 3/2002 | Manushakian | | 6,837,847 B2 | 1/2005 | Ewers et al. |
| 6,371,956 B1 | 4/2002 | Wilson et al. | | 6,843,794 B2 | 1/2005 | Sixto, Jr. et al. |
| 6,379,366 B1 | 4/2002 | Fleischman et al. | | 6,861,250 B1 | 3/2005 | Cole et al. |
| 6,383,195 B1 | 5/2002 | Richard | | 6,866,627 B2 | 3/2005 | Nozue |
| 6,383,197 B1 | 5/2002 | Conlon et al. | | 6,878,106 B1 | 4/2005 | Herrmann |
| 6,391,029 B1 | 5/2002 | Hooven et al. | | 6,878,110 B2 | 4/2005 | Yang et al. |
| 6,406,440 B1 | 6/2002 | Stefanchik | | 6,884,213 B2 | 4/2005 | Raz et al. |
| 6,409,733 B1 | 6/2002 | Conlon et al. | | 6,887,255 B2 | 5/2005 | Shimm |
| 6,431,500 B1 | 8/2002 | Jacobs et al. | | 6,896,683 B1 | 5/2005 | Gadberry et al. |
| 6,447,511 B1 | 9/2002 | Slater | | 6,908,427 B2 | 6/2005 | Fleener et al. |
| 6,447,523 B1 | 9/2002 | Middleman et al. | | 6,908,476 B2 | 6/2005 | Jud et al. |
| 6,454,783 B1 | 9/2002 | Piskun | | 6,916,284 B2 | 7/2005 | Moriyama |
| 6,454,785 B2 | 9/2002 | De Hoyos Garza | | 6,918,871 B2 | 7/2005 | Schulze |
| 6,464,701 B1 | 10/2002 | Hooven et al. | | 6,926,725 B2 | 8/2005 | Cooke et al. |
| 6,475,104 B1 | 11/2002 | Lutz et al. | | 6,932,810 B2 | 8/2005 | Ryan |
| 6,485,411 B1 | 11/2002 | Konstorum et al. | | 6,932,824 B1 | 8/2005 | Roop et al. |
| 6,489,745 B1 | 12/2002 | Koreis | | 6,932,827 B2 | 8/2005 | Cole |
| 6,491,626 B1 | 12/2002 | Stone et al. | | 6,942,613 B2 | 9/2005 | Ewers et al. |
| 6,491,691 B1 | 12/2002 | Morley et al. | | 6,945,472 B2 | 9/2005 | Wuttke et al. |
| 6,494,893 B2 | 12/2002 | Dubrul et al. | | 6,945,979 B2 | 9/2005 | Kortenbach et al. |
| 6,503,192 B1 | 1/2003 | Ouchi | | 6,958,035 B2 | 10/2005 | Friedman et al. |
| 6,506,190 B1 | 1/2003 | Walshe | | 6,960,162 B2 | 11/2005 | Saadat et al. |
| 6,508,827 B1 | 1/2003 | Manhes | | 6,960,163 B2 | 11/2005 | Ewers et al. |
| 6,543,456 B1 | 4/2003 | Freeman | | 6,962,587 B2 | 11/2005 | Johnson et al. |
| 6,551,270 B1 | 4/2003 | Bimbo et al. | | 6,964,662 B2 | 11/2005 | Kidooka |
| 6,554,829 B2 | 4/2003 | Schulze et al. | | 6,966,909 B2 | 11/2005 | Marshall et al. |
| 6,558,384 B2 | 5/2003 | Mayenberger | | 6,966,919 B2 | 11/2005 | Sixto, Jr. et al. |
| 6,562,035 B1 | 5/2003 | Levin | | 6,967,462 B1 | 11/2005 | Landis |
| 6,562,052 B2 | 5/2003 | Nobles et al. | | 6,971,988 B2 | 12/2005 | Orban, III |
| 6,569,159 B1 | 5/2003 | Edwards et al. | | 6,972,017 B2 | 12/2005 | Smith et al. |
| 6,572,629 B2 | 6/2003 | Kalloo et al. | | 6,974,411 B2 | 12/2005 | Belson |
| 6,572,635 B1 | 6/2003 | Bonutti | | 6,976,992 B2 | 12/2005 | Sachatello et al. |
| 6,575,988 B2 | 6/2003 | Rousseau | | 6,984,203 B2 | 1/2006 | Tartaglia et al. |
| 6,579,311 B1 | 6/2003 | Makower | | 6,984,205 B2 | 1/2006 | Gazdzinski |

| | | |
|---|---|---|
| 6,986,774 B2 | 1/2006 | Middleman et al. |
| 6,988,987 B2 | 1/2006 | Ishikawa et al. |
| 6,991,627 B2 | 1/2006 | Madhani et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,008,375 B2 | 3/2006 | Weisel |
| 7,009,634 B2 | 3/2006 | Iddan et al. |
| 7,010,340 B2 | 3/2006 | Scarantino et al. |
| 7,020,531 B1 | 3/2006 | Colliou et al. |
| 7,025,580 B2 | 4/2006 | Heagy et al. |
| 7,029,435 B2 | 4/2006 | Nakao |
| 7,029,438 B2 | 4/2006 | Morin et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,629 B2 | 8/2006 | Weller et al. |
| 7,087,071 B2 | 8/2006 | Nicholas et al. |
| 7,090,673 B2 | 8/2006 | Dycus et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,703 B2 | 9/2006 | Danitz et al. |
| 7,112,208 B2 | 9/2006 | Morris et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| RE39,415 E | 11/2006 | Bales et al. |
| 7,131,978 B2 | 11/2006 | Sancoff et al. |
| 7,131,979 B2 * | 11/2006 | DiCarlo et al. ............... 606/144 |
| 7,131,980 B1 * | 11/2006 | Field et al. .................... 606/146 |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,153,321 B2 | 12/2006 | Andrews |
| 7,163,525 B2 | 1/2007 | Franer |
| 7,172,714 B2 | 2/2007 | Jacobson |
| 7,179,254 B2 | 2/2007 | Pendekanti et al. |
| 7,195,612 B2 | 3/2007 | Van Sloten et al. |
| 7,195,631 B2 | 3/2007 | Dumbauld |
| 7,208,005 B2 | 4/2007 | Frecker et al. |
| 7,211,092 B2 | 5/2007 | Hughett |
| 7,223,272 B2 | 5/2007 | Francere et al. |
| 7,232,414 B2 | 6/2007 | Gonzalez |
| 7,232,445 B2 | 6/2007 | Kortenbach et al. |
| 7,241,290 B2 | 7/2007 | Doyle et al. |
| 7,244,228 B2 | 7/2007 | Lubowski |
| 7,252,660 B2 | 8/2007 | Kunz |
| 7,270,663 B2 | 9/2007 | Nakao |
| 7,294,139 B1 | 11/2007 | Gengler |
| 7,301,250 B2 | 11/2007 | Cassel |
| 7,306,597 B2 | 12/2007 | Manzo |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,257 B2 | 2/2008 | Kanehira et al. |
| 7,329,383 B2 | 2/2008 | Stinson |
| 7,344,536 B1 | 3/2008 | Lunsford et al. |
| 7,364,582 B2 | 4/2008 | Lee |
| 7,371,215 B2 | 5/2008 | Colliou et al. |
| 7,381,216 B2 | 6/2008 | Buzzard et al. |
| 7,393,322 B2 | 7/2008 | Wenchell |
| 7,402,162 B2 | 7/2008 | Ouchi |
| 7,404,791 B2 | 7/2008 | Linares et al. |
| 7,416,554 B2 * | 8/2008 | Lam et al. ..................... 606/153 |
| 7,422,590 B2 | 9/2008 | Kupferschmid et al. |
| 7,455,208 B2 | 11/2008 | Wales et al. |
| 7,488,295 B2 | 2/2009 | Burbank et al. |
| 7,497,867 B2 | 3/2009 | Lasner et al. |
| 7,507,200 B2 | 3/2009 | Okada |
| 7,524,281 B2 | 4/2009 | Chu et al. |
| 7,534,228 B2 | 5/2009 | Williams |
| 7,544,203 B2 | 6/2009 | Chin et al. |
| 7,548,040 B2 | 6/2009 | Lee et al. |
| 7,549,564 B2 | 6/2009 | Boudreaux |
| 7,553,278 B2 | 6/2009 | Kucklick |
| 7,553,298 B2 | 6/2009 | Hunt et al. |
| 7,559,887 B2 | 7/2009 | Dannan |
| 7,561,916 B2 | 7/2009 | Hunt et al. |
| 7,566,334 B2 | 7/2009 | Christian et al. |
| 7,575,144 B2 | 8/2009 | Ortiz et al. |
| 7,579,550 B2 | 8/2009 | Dayton et al. |
| 7,582,096 B2 * | 9/2009 | Gellman et al. ............... 606/144 |
| 7,588,177 B2 | 9/2009 | Racenet |
| 7,632,250 B2 | 12/2009 | Smith et al. |
| 7,635,373 B2 | 12/2009 | Ortiz |
| 7,651,483 B2 | 1/2010 | Byrum et al. |
| 7,651,509 B2 | 1/2010 | Bojarski et al. |
| 7,654,431 B2 | 2/2010 | Hueil et al. |
| 7,662,089 B2 | 2/2010 | Okada et al. |
| 7,666,180 B2 | 2/2010 | Holsten et al. |
| 7,713,270 B2 | 5/2010 | Suzuki |
| 7,736,374 B2 | 6/2010 | Vaughan et al. |
| 7,762,998 B2 | 7/2010 | Birk et al. |
| 7,780,683 B2 | 8/2010 | Roue et al. |
| 7,794,475 B2 | 9/2010 | Hess et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,867,216 B2 | 1/2011 | Wahr et al. |
| 7,918,869 B2 | 4/2011 | Saadat et al. |
| 7,931,624 B2 | 4/2011 | Smith et al. |
| 7,955,298 B2 | 6/2011 | Carroll et al. |
| 2001/0049497 A1 | 12/2001 | Kalloo et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0091391 A1 | 7/2002 | Cole et al. |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0183591 A1 | 12/2002 | Matsuura et al. |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0114732 A1 | 6/2003 | Webler et al. |
| 2003/0130564 A1 | 7/2003 | Martone et al. |
| 2003/0130656 A1 | 7/2003 | Levin |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0191497 A1 | 10/2003 | Cope |
| 2003/0195565 A1 | 10/2003 | Bonutti |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002735 A1 | 1/2004 | Lizardi et al. |
| 2004/0034369 A1 | 2/2004 | Sauer et al. |
| 2004/0098007 A1 | 5/2004 | Heiss |
| 2004/0101456 A1 | 5/2004 | Kuroshima et al. |

| | | | | | | |
|---|---|---|---|---|---|---|
| 2004/0116948 A1 | 6/2004 | Sixto, Jr. et al. | | 2005/0273084 A1 | 12/2005 | Hinman et al. |
| 2004/0133077 A1 | 7/2004 | Obenchain et al. | | 2005/0277945 A1 | 12/2005 | Saadat et al. |
| 2004/0133089 A1 | 7/2004 | Kilcoyne et al. | | 2005/0277951 A1 | 12/2005 | Smith et al. |
| 2004/0136779 A1 | 7/2004 | Bhaskar | | 2005/0277952 A1 | 12/2005 | Arp et al. |
| 2004/0138525 A1 | 7/2004 | Saadat et al. | | 2005/0277954 A1 | 12/2005 | Smith et al. |
| 2004/0138529 A1 | 7/2004 | Wiltshire et al. | | 2005/0277955 A1 | 12/2005 | Palmer et al. |
| 2004/0138587 A1 | 7/2004 | Lyons, IV | | 2005/0277956 A1 | 12/2005 | Francese et al. |
| 2004/0186350 A1 | 9/2004 | Brenneman et al. | | 2005/0277957 A1 | 12/2005 | Kuhns et al. |
| 2004/0193009 A1 | 9/2004 | Jaffe et al. | | 2005/0283118 A1 | 12/2005 | Uth et al. |
| 2004/0193146 A1 | 9/2004 | Lee et al. | | 2005/0283119 A1 | 12/2005 | Uth et al. |
| 2004/0193186 A1 | 9/2004 | Kortenbach et al. | | 2005/0288555 A1 | 12/2005 | Binmoeller |
| 2004/0193188 A1 | 9/2004 | Francese | | 2006/0004406 A1 | 1/2006 | Wehrstein et al. |
| 2004/0193189 A1 | 9/2004 | Kortenbach et al. | | 2006/0004409 A1 | 1/2006 | Nobis et al. |
| 2004/0193200 A1 | 9/2004 | Dworschak et al. | | 2006/0004410 A1 | 1/2006 | Nobis et al. |
| 2004/0199052 A1 | 10/2004 | Banik et al. | | 2006/0015009 A1 | 1/2006 | Jaffe et al. |
| 2004/0210245 A1 | 10/2004 | Erickson et al. | | 2006/0020167 A1 | 1/2006 | Sitzmann |
| 2004/0215058 A1 | 10/2004 | Zirps et al. | | 2006/0020247 A1 | 1/2006 | Kagan et al. |
| 2004/0225183 A1 | 11/2004 | Michlitsch et al. | | 2006/0025654 A1 | 2/2006 | Suzuki et al. |
| 2004/0225186 A1 | 11/2004 | Horne, Jr. et al. | | 2006/0025781 A1 | 2/2006 | Young et al. |
| 2004/0230095 A1 | 11/2004 | Stefanchik et al. | | 2006/0025812 A1 | 2/2006 | Shelton, IV |
| 2004/0230096 A1 | 11/2004 | Stefanchik et al. | | 2006/0025819 A1 | 2/2006 | Nobis et al. |
| 2004/0230097 A1 | 11/2004 | Stefanchik et al. | | 2006/0036267 A1 | 2/2006 | Saadat et al. |
| 2004/0230161 A1 | 11/2004 | Zeiner | | 2006/0041188 A1 | 2/2006 | Dirusso et al. |
| 2004/0249246 A1 | 12/2004 | Campos | | 2006/0058582 A1 | 3/2006 | Maahs et al. |
| 2004/0249367 A1 | 12/2004 | Saadat et al. | | 2006/0058776 A1 | 3/2006 | Bilsbury |
| 2004/0249394 A1* | 12/2004 | Morris et al. .................. 606/144 | | 2006/0069396 A1* | 3/2006 | Meade et al. .................. 606/144 |
| 2005/0033277 A1 | 2/2005 | Clague et al. | | 2006/0074413 A1 | 4/2006 | Behzadian |
| 2005/0033319 A1 | 2/2005 | Gambale et al. | | 2006/0079890 A1 | 4/2006 | Guerra |
| 2005/0033333 A1 | 2/2005 | Smith et al. | | 2006/0089528 A1 | 4/2006 | Tartaglia et al. |
| 2005/0043690 A1 | 2/2005 | Todd | | 2006/0095060 A1 | 5/2006 | Mayenberger et al. |
| 2005/0049616 A1 | 3/2005 | Rivera et al. | | 2006/0106423 A1 | 5/2006 | Weisel et al. |
| 2005/0065397 A1 | 3/2005 | Saadat et al. | | 2006/0111209 A1 | 5/2006 | Hinman et al. |
| 2005/0065517 A1 | 3/2005 | Chin | | 2006/0111210 A1 | 5/2006 | Hinman et al. |
| 2005/0070754 A1 | 3/2005 | Nobis et al. | | 2006/0111704 A1 | 5/2006 | Brenneman et al. |
| 2005/0070763 A1 | 3/2005 | Nobis et al. | | 2006/0129166 A1 | 6/2006 | Lavelle |
| 2005/0070764 A1 | 3/2005 | Nobis et al. | | 2006/0135962 A1 | 6/2006 | Kick et al. |
| 2005/0080413 A1 | 4/2005 | Canady | | 2006/0135971 A1 | 6/2006 | Swanstrom et al. |
| 2005/0085693 A1 | 4/2005 | Belson et al. | | 2006/0135984 A1 | 6/2006 | Kramer et al. |
| 2005/0085832 A1 | 4/2005 | Sancoff et al. | | 2006/0142644 A1 | 6/2006 | Mulac et al. |
| 2005/0090837 A1 | 4/2005 | Sixto, Jr. et al. | | 2006/0142652 A1 | 6/2006 | Keenan |
| 2005/0090838 A1 | 4/2005 | Sixto, Jr. et al. | | 2006/0142790 A1 | 6/2006 | Gertner |
| 2005/0101837 A1 | 5/2005 | Kalloo et al. | | 2006/0142798 A1 | 6/2006 | Holman et al. |
| 2005/0101838 A1 | 5/2005 | Camillocci et al. | | 2006/0149132 A1 | 7/2006 | Iddan |
| 2005/0107663 A1 | 5/2005 | Saadat et al. | | 2006/0149135 A1 | 7/2006 | Paz |
| 2005/0107664 A1 | 5/2005 | Kalloo et al. | | 2006/0161190 A1 | 7/2006 | Gadberry et al. |
| 2005/0110881 A1 | 5/2005 | Glukhovsky et al. | | 2006/0167416 A1 | 7/2006 | Mathis et al. |
| 2005/0113847 A1 | 5/2005 | Gadberry et al. | | 2006/0167482 A1 | 7/2006 | Swain et al. |
| 2005/0124855 A1 | 6/2005 | Jaffe et al. | | 2006/0178560 A1 | 8/2006 | Saadat et al. |
| 2005/0125010 A1 | 6/2005 | Smith et al. | | 2006/0183975 A1 | 8/2006 | Saadat et al. |
| 2005/0131279 A1 | 6/2005 | Boulais et al. | | 2006/0184161 A1 | 8/2006 | Maahs et al. |
| 2005/0131457 A1 | 6/2005 | Douglas et al. | | 2006/0189844 A1 | 8/2006 | Tien |
| 2005/0137454 A1 | 6/2005 | Saadat et al. | | 2006/0189845 A1 | 8/2006 | Maahs et al. |
| 2005/0143647 A1 | 6/2005 | Minai et al. | | 2006/0190027 A1 | 8/2006 | Downey |
| 2005/0143690 A1 | 6/2005 | High | | 2006/0195084 A1 | 8/2006 | Slater |
| 2005/0143774 A1 | 6/2005 | Polo | | 2006/0200005 A1 | 9/2006 | Bjork et al. |
| 2005/0149087 A1 | 7/2005 | Ahlberg et al. | | 2006/0200169 A1 | 9/2006 | Sniffin |
| 2005/0149096 A1 | 7/2005 | Hilal et al. | | 2006/0200170 A1 | 9/2006 | Aranyi |
| 2005/0159648 A1 | 7/2005 | Freed | | 2006/0200199 A1 | 9/2006 | Bonutti et al. |
| 2005/0165272 A1 | 7/2005 | Okada et al. | | 2006/0217665 A1 | 9/2006 | Prosek |
| 2005/0165378 A1 | 7/2005 | Heinrich et al. | | 2006/0217697 A1 | 9/2006 | Lau et al. |
| 2005/0165411 A1 | 7/2005 | Orban, III | | 2006/0217742 A1 | 9/2006 | Messerly et al. |
| 2005/0165429 A1 | 7/2005 | Douglas et al. | | 2006/0217743 A1 | 9/2006 | Messerly et al. |
| 2005/0182429 A1 | 8/2005 | Yamanouchi | | 2006/0229639 A1 | 10/2006 | Whitfield |
| 2005/0192478 A1 | 9/2005 | Williams et al. | | 2006/0229640 A1 | 10/2006 | Whitfield |
| 2005/0192598 A1 | 9/2005 | Johnson et al. | | 2006/0237022 A1 | 10/2006 | Chen et al. |
| 2005/0192602 A1 | 9/2005 | Manzo | | 2006/0237023 A1 | 10/2006 | Cox et al. |
| 2005/0192654 A1 | 9/2005 | Chanduszko et al. | | 2006/0241570 A1 | 10/2006 | Wilk |
| 2005/0209624 A1 | 9/2005 | Vijay | | 2006/0247673 A1 | 11/2006 | Voegele et al. |
| 2005/0215858 A1 | 9/2005 | Vail, III | | 2006/0253004 A1 | 11/2006 | Frisch et al. |
| 2005/0216050 A1 | 9/2005 | Sepetka et al. | | 2006/0253039 A1 | 11/2006 | McKenna et al. |
| 2005/0228406 A1 | 10/2005 | Bose | | 2006/0258907 A1 | 11/2006 | Stefanchik et al. |
| 2005/0234297 A1 | 10/2005 | Devierre et al. | | 2006/0258908 A1 | 11/2006 | Stefanchik et al. |
| 2005/0250990 A1 | 11/2005 | Le et al. | | 2006/0258910 A1 | 11/2006 | Stefanchik et al. |
| 2005/0250993 A1 | 11/2005 | Jaeger | | 2006/0258954 A1 | 11/2006 | Timberlake et al. |
| 2005/0251176 A1 | 11/2005 | Swanstrom et al. | | 2006/0258955 A1 | 11/2006 | Hoffman et al. |
| 2005/0261674 A1 | 11/2005 | Nobis et al. | | 2006/0259010 A1 | 11/2006 | Stefanchik et al. |
| 2005/0267492 A1 | 12/2005 | Poncet et al. | | 2006/0264752 A1 | 11/2006 | Rubinsky et al. |
| 2005/0272975 A1 | 12/2005 | McWeeney et al. | | 2006/0264930 A1 | 11/2006 | Nishimura |
| 2005/0272977 A1 | 12/2005 | Saadat et al. | | 2006/0270902 A1 | 11/2006 | Igarashi et al. |

| | | | | | | |
|---|---|---|---|---|---|---|
| 2006/0271102 A1 | 11/2006 | Bosshard et al. | | 2008/0097472 A1 | 4/2008 | Agmon et al. |
| 2006/0276835 A1 | 12/2006 | Uchida | | 2008/0097483 A1 | 4/2008 | Ortiz et al. |
| 2006/0281970 A1 | 12/2006 | Stokes et al. | | 2008/0103527 A1 | 5/2008 | Martin et al. |
| 2006/0282106 A1 | 12/2006 | Cole et al. | | 2008/0114384 A1 | 5/2008 | Chang et al. |
| 2006/0285732 A1 | 12/2006 | Horn et al. | | 2008/0119870 A1 | 5/2008 | Williams |
| 2006/0287644 A1 | 12/2006 | Inganas et al. | | 2008/0125796 A1 | 5/2008 | Graham |
| 2006/0287666 A1 | 12/2006 | Saadat et al. | | 2008/0132892 A1 | 6/2008 | Lunsford et al. |
| 2006/0293626 A1 | 12/2006 | Byrum et al. | | 2008/0139882 A1 | 6/2008 | Fujimori |
| 2007/0002135 A1 | 1/2007 | Glukhovsky | | 2008/0147113 A1 | 6/2008 | Nobis et al. |
| 2007/0005019 A1 | 1/2007 | Okishige | | 2008/0171907 A1 | 7/2008 | Long et al. |
| 2007/0015965 A1 | 1/2007 | Cox et al. | | 2008/0188868 A1 | 8/2008 | Weitzner et al. |
| 2007/0016225 A1 | 1/2007 | Nakao | | 2008/0200755 A1 | 8/2008 | Bakos |
| 2007/0032700 A1 | 2/2007 | Fowler et al. | | 2008/0200762 A1 | 8/2008 | Stokes et al. |
| 2007/0032701 A1 | 2/2007 | Fowler et al. | | 2008/0200911 A1 | 8/2008 | Long |
| 2007/0043345 A1 | 2/2007 | Davalos et al. | | 2008/0200912 A1 | 8/2008 | Long |
| 2007/0049800 A1 | 3/2007 | Boulais | | 2008/0200933 A1 | 8/2008 | Bakos et al. |
| 2007/0051375 A1 | 3/2007 | Milliman | | 2008/0200934 A1 | 8/2008 | Fox |
| 2007/0060880 A1 | 3/2007 | Gregorich et al. | | 2008/0208213 A1 | 8/2008 | Benjamin et al. |
| 2007/0073102 A1 | 3/2007 | Matsuno et al. | | 2008/0221587 A1 | 9/2008 | Schwartz |
| 2007/0073269 A1 | 3/2007 | Becker | | 2008/0221619 A1 | 9/2008 | Spivey et al. |
| 2007/0079924 A1 | 4/2007 | Saadat et al. | | 2008/0228213 A1 | 9/2008 | Blakeney et al. |
| 2007/0088370 A1 | 4/2007 | Kahle et al. | | 2008/0230972 A1 | 9/2008 | Ganley |
| 2007/0100375 A1 | 5/2007 | Mikkaichi et al. | | 2008/0234696 A1 | 9/2008 | Taylor et al. |
| 2007/0100376 A1 | 5/2007 | Mikkaichi et al. | | 2008/0243106 A1 | 10/2008 | Coe et al. |
| 2007/0106118 A1 | 5/2007 | Moriyama | | 2008/0243148 A1 | 10/2008 | Mikkaichi et al. |
| 2007/0112251 A1 | 5/2007 | Nakhuda | | 2008/0243176 A1 | 10/2008 | Weitzner et al. |
| 2007/0112331 A1 | 5/2007 | Weber et al. | | 2008/0262540 A1 | 10/2008 | Bangera et al. |
| 2007/0112342 A1 | 5/2007 | Pearson et al. | | 2008/0269782 A1 | 10/2008 | Stefanchik et al. |
| 2007/0112383 A1 | 5/2007 | Conlon et al. | | 2008/0275474 A1 | 11/2008 | Martin et al. |
| 2007/0112384 A1 | 5/2007 | Conlon et al. | | 2008/0275475 A1 | 11/2008 | Schwemberger et al. |
| 2007/0112385 A1 | 5/2007 | Conlon | | 2008/0287737 A1 | 11/2008 | Dejima |
| 2007/0112425 A1 | 5/2007 | Schaller et al. | | 2008/0300547 A1 | 12/2008 | Bakos |
| 2007/0118115 A1 | 5/2007 | Artale et al. | | 2008/0309758 A1 | 12/2008 | Karasawa et al. |
| 2007/0123840 A1 | 5/2007 | Cox | | 2008/0312496 A1 | 12/2008 | Zwolinski |
| 2007/0129605 A1 | 6/2007 | Schaaf | | 2008/0312499 A1 | 12/2008 | Handa et al. |
| 2007/0129719 A1 | 6/2007 | Kendale et al. | | 2008/0312500 A1 | 12/2008 | Asada et al. |
| 2007/0135709 A1 | 6/2007 | Rioux et al. | | 2008/0312506 A1 | 12/2008 | Spivey et al. |
| 2007/0142706 A1 | 6/2007 | Matsui et al. | | 2008/0319436 A1 | 12/2008 | Daniel et al. |
| 2007/0156127 A1 | 7/2007 | Rioux et al. | | 2008/0319439 A1 | 12/2008 | Ootsubu |
| 2007/0161855 A1 | 7/2007 | Mikkaichi et al. | | 2009/0054728 A1 | 2/2009 | Trusty |
| 2007/0173691 A1 | 7/2007 | Yokoi et al. | | 2009/0062788 A1 | 3/2009 | Long et al. |
| 2007/0173869 A1 | 7/2007 | Gannoe et al. | | 2009/0062792 A1 | 3/2009 | Vakharia et al. |
| 2007/0173870 A2 | 7/2007 | Zacharias | | 2009/0062795 A1 | 3/2009 | Vakharia et al. |
| 2007/0173872 A1 | 7/2007 | Neuenfeldt | | 2009/0069634 A1 | 3/2009 | Larkin |
| 2007/0179525 A1 | 8/2007 | Frecker et al. | | 2009/0076499 A1 | 3/2009 | Azure |
| 2007/0179530 A1 | 8/2007 | Tieu et al. | | 2009/0082776 A1 | 3/2009 | Cresina |
| 2007/0197865 A1 | 8/2007 | Miyake et al. | | 2009/0082779 A1 | 3/2009 | Nakao |
| 2007/0203487 A1 | 8/2007 | Sugita | | 2009/0112059 A1 | 4/2009 | Nobis |
| 2007/0208364 A1 | 9/2007 | Smith et al. | | 2009/0112062 A1 | 4/2009 | Bakos |
| 2007/0213754 A1 | 9/2007 | Mikkaichi et al. | | 2009/0112063 A1 | 4/2009 | Bakos et al. |
| 2007/0225554 A1 | 9/2007 | Maseda et al. | | 2009/0131751 A1 | 5/2009 | Spivey et al. |
| 2007/0233040 A1 | 10/2007 | Macnamara et al. | | 2009/0131932 A1 | 5/2009 | Vakharia et al. |
| 2007/0244358 A1 | 10/2007 | Lee | | 2009/0131933 A1 | 5/2009 | Ghabrial et al. |
| 2007/0250057 A1 | 10/2007 | Nobis et al. | | 2009/0143639 A1 | 6/2009 | Stark |
| 2007/0255096 A1 | 11/2007 | Stefanchik et al. | | 2009/0143649 A1 | 6/2009 | Rossi |
| 2007/0255100 A1 | 11/2007 | Barlow et al. | | 2009/0143794 A1 | 6/2009 | Conlon et al. |
| 2007/0255273 A1 | 11/2007 | Fernandez et al. | | 2009/0149710 A1 | 6/2009 | Stefanchik et al. |
| 2007/0255303 A1 | 11/2007 | Bakos et al. | | 2009/0177031 A1 | 7/2009 | Surti et al. |
| 2007/0255306 A1 | 11/2007 | Conlon et al. | | 2009/0177219 A1 | 7/2009 | Conlon |
| 2007/0260112 A1 | 11/2007 | Rahmani | | 2009/0182332 A1 | 7/2009 | Long et al. |
| 2007/0260117 A1 | 11/2007 | Zwolinski et al. | | 2009/0192344 A1 | 7/2009 | Bakos et al. |
| 2007/0260121 A1 | 11/2007 | Bakos et al. | | 2009/0198231 A1 | 8/2009 | Esser et al. |
| 2007/0260273 A1 | 11/2007 | Cropper et al. | | 2009/0227828 A1 | 9/2009 | Swain et al. |
| 2007/0270629 A1 | 11/2007 | Charles | | 2009/0248055 A1 | 10/2009 | Spivey et al. |
| 2007/0270889 A1 | 11/2007 | Conlon et al. | | 2009/0281559 A1 | 11/2009 | Swain et al. |
| 2007/0270895 A1 | 11/2007 | Nobis et al. | | 2009/0287236 A1 | 11/2009 | Bakos et al. |
| 2007/0270907 A1 | 11/2007 | Stokes et al. | | 2009/0292164 A1 | 11/2009 | Yamatani |
| 2007/0282371 A1 | 12/2007 | Lee et al. | | 2009/0299135 A1 | 12/2009 | Spivey |
| 2007/0299387 A1 | 12/2007 | Williams et al. | | 2009/0299143 A1 | 12/2009 | Conlon et al. |
| 2008/0004650 A1 | 1/2008 | George | | 2009/0299362 A1 | 12/2009 | Long et al. |
| 2008/0015409 A1 | 1/2008 | Barlow et al. | | 2009/0299385 A1 | 12/2009 | Stefanchik et al. |
| 2008/0015552 A1 | 1/2008 | Doyle et al. | | 2009/0299406 A1 | 12/2009 | Swain et al. |
| 2008/0027387 A1 | 1/2008 | Grabinsky | | 2009/0299409 A1 | 12/2009 | Coe et al. |
| 2008/0033451 A1 | 2/2008 | Rieber et al. | | 2009/0306658 A1 | 12/2009 | Nobis et al. |
| 2008/0051629 A1 | 2/2008 | Sugiyama et al. | | 2009/0306683 A1 | 12/2009 | Zwolinski et al. |
| 2008/0051735 A1 | 2/2008 | Measamer et al. | | 2009/0322864 A1 | 12/2009 | Karasawa et al. |
| 2008/0058586 A1 | 3/2008 | Karpiel | | 2009/0326561 A1 | 12/2009 | Carroll, II et al. |
| 2008/0065169 A1 | 3/2008 | Colliou et al. | | 2010/0010294 A1 | 1/2010 | Conlon et al. |
| 2008/0086172 A1 | 4/2008 | Martin et al. | | 2010/0010298 A1 | 1/2010 | Bakos et al. |

| | | | | | | |
|---|---|---|---|---|---|---|
| 2010/0010299 A1 | 1/2010 | Bakos et al. | EP | 1568330 A1 | 8/2005 | |
| 2010/0010303 A1 | 1/2010 | Bakos | EP | 1452143 B1 | 9/2005 | |
| 2010/0010510 A1 | 1/2010 | Stefanchik | EP | 1616527 A2 | 1/2006 | |
| 2010/0010511 A1 | 1/2010 | Harris et al. | EP | 1006888 B1 | 3/2006 | |
| 2010/0023032 A1 | 1/2010 | Granja Filho | EP | 1629764 A1 | 3/2006 | |
| 2010/0042045 A1 | 2/2010 | Spivey | EP | 1013229 B1 | 6/2006 | |
| 2010/0048990 A1 | 2/2010 | Bakos | EP | 1721561 A1 | 11/2006 | |
| 2010/0049190 A1 | 2/2010 | Long et al. | EP | 1153578 B1 | 3/2007 | |
| 2010/0049223 A1 | 2/2010 | Granja Filho | EP | 1334696 B1 | 3/2007 | |
| 2010/0056861 A1 | 3/2010 | Spivey | EP | 1769766 A1 | 4/2007 | |
| 2010/0056862 A1 | 3/2010 | Bakos | EP | 1836971 A2 | 9/2007 | |
| 2010/0057085 A1 | 3/2010 | Holcomb et al. | EP | 1836980 A1 | 9/2007 | |
| 2010/0057108 A1 | 3/2010 | Spivey et al. | EP | 1854421 A2 | 11/2007 | |
| 2010/0063538 A1 | 3/2010 | Spivey et al. | EP | 1857061 A1 | 11/2007 | |
| 2010/0076451 A1 | 3/2010 | Zwolinski et al. | EP | 1875876 A1 | 1/2008 | |
| 2010/0081877 A1 | 4/2010 | Vakharia | EP | 1891881 A1 | 2/2008 | |
| 2010/0087813 A1 | 4/2010 | Long | EP | 1902663 A1 | 3/2008 | |
| 2010/0113872 A1 | 5/2010 | Asada et al. | EP | 1477106 B1 | 6/2008 | |
| 2010/0121362 A1 | 5/2010 | Clague et al. | EP | 1949844 A1 | 7/2008 | |
| 2010/0130817 A1 | 5/2010 | Conlon | EP | 1518499 B1 | 8/2008 | |
| 2010/0130975 A1 | 5/2010 | Long | EP | 1709918 B1 | 10/2008 | |
| 2010/0131005 A1 | 5/2010 | Conlon | EP | 1985226 A2 | 10/2008 | |
| 2010/0152539 A1 | 6/2010 | Ghabrial et al. | EP | 1994904 A1 | 11/2008 | |
| 2010/0152609 A1 | 6/2010 | Zwolinski et al. | EP | 1707130 B1 | 12/2008 | |
| 2010/0152746 A1 | 6/2010 | Ceniccola et al. | EP | 1769749 B1 | 11/2009 | |
| 2010/0179510 A1 | 7/2010 | Fox et al. | FR | 2731610 A1 | 9/1996 | |
| 2010/0179530 A1 | 7/2010 | Long et al. | GB | 330629 A | 6/1930 | |
| 2010/0191050 A1 | 7/2010 | Zwolinski | GB | 2403909 A | 1/2005 | |
| 2010/0191267 A1 | 7/2010 | Fox | GB | 2421190 A | 6/2006 | |
| 2010/0198005 A1 | 8/2010 | Fox | GB | 2443261 A | 4/2008 | |
| 2010/0198149 A1 | 8/2010 | Fox | JP | 56-46674 | 4/1981 | |
| 2010/0198244 A1 | 8/2010 | Spivey et al. | JP | 8-29699 A | 2/1996 | |
| 2010/0198248 A1 | 8/2010 | Vakharia | JP | 2002-369791 A | 12/2002 | |
| 2010/0249700 A1 | 9/2010 | Spivey | JP | 2003-088494 A | 3/2003 | |
| 2010/0286791 A1 | 11/2010 | Goldsmith | JP | 2003-235852 A | 8/2003 | |
| 2010/0298642 A1 | 11/2010 | Trusty et al. | JP | 2004-33525 A | 2/2004 | |
| 2010/0331622 A2 | 12/2010 | Conlon | JP | 2004-065745 A | 3/2004 | |
| 2010/0331774 A2 | 12/2010 | Spivey | JP | 2005-121947 A | 5/2005 | |
| 2011/0093009 A1 | 4/2011 | Fox | JP | 2005-261514 A | 9/2005 | |
| 2011/0098694 A1 | 4/2011 | Long | NL | 1021295 C2 | 2/2004 | |
| 2011/0098704 A1 | 4/2011 | Long et al. | SU | 194230 | 5/1967 | |
| 2011/0105850 A1 | 5/2011 | Voegele et al. | SU | 980703 | 12/1982 | |
| 2011/0112434 A1 | 5/2011 | Ghabrial et al. | WO | WO 84/01707 A1 | 5/1984 | |
| 2011/0115891 A1 | 5/2011 | Trusty | WO | WO 92/13494 A1 | 8/1992 | |
| 2011/0124964 A1 | 5/2011 | Nobis | WO | WO 93/10850 A1 | 6/1993 | |
| 2011/0152609 A1 | 6/2011 | Trusty et al. | WO | WO 93/20760 A1 | 10/1993 | |
| 2011/0152610 A1 | 6/2011 | Trusty et al. | WO | WO 93/20765 A1 | 10/1993 | |
| 2011/0152612 A1 | 6/2011 | Trusty et al. | WO | WO 95/09666 A1 | 4/1995 | |
| 2011/0152858 A1 | 6/2011 | Long et al. | WO | WO 96/22056 A1 | 7/1996 | |
| 2011/0152859 A1 | 6/2011 | Long et al. | WO | WO 96/27331 A1 | 9/1996 | |
| 2011/0152878 A1 | 6/2011 | Trusty et al. | WO | WO 96/39946 A1 | 12/1996 | |
| 2011/0152923 A1 | 6/2011 | Fox | WO | WO 97/12557 A1 | 4/1997 | |
| 2011/0160514 A1 | 6/2011 | Long et al. | WO | WO 98/01080 A1 | 1/1998 | |
| | | | WO | WO 99/09919 A1 | 3/1999 | |
| FOREIGN PATENT DOCUMENTS | | | WO | WO 99/17661 A1 | 4/1999 | |
| DE | 3008120 A1 | 9/1980 | WO | WO 99/30622 A2 | 6/1999 | |
| DE | 4323585 A1 | 1/1995 | WO | WO 01/10319 A1 | 2/2001 | |
| DE | 19757056 B4 | 8/2008 | WO | WO 01/41627 A2 | 6/2001 | |
| DE | 102006027873 B4 | 10/2009 | WO | WO 01/58360 A2 | 8/2001 | |
| EP | 0086338 A1 | 8/1983 | WO | WO 02/11621 A1 | 2/2002 | |
| EP | 0286415 A2 | 10/1988 | WO | WO 02/34122 A2 | 5/2002 | |
| EP | 0589454 A2 | 3/1994 | WO | WO 02/094082 A2 | 11/2002 | |
| EP | 0464479 B1 | 3/1995 | WO | WO 03/045260 A1 | 6/2003 | |
| EP | 0529675 B1 | 2/1996 | WO | WO 03/047684 A2 | 6/2003 | |
| EP | 0724863 B1 | 7/1999 | WO | WO 03/059412 A2 | 7/2003 | |
| EP | 0760629 B1 | 11/1999 | WO | WO 03/078721 A2 | 9/2003 | |
| EP | 0818974 B1 | 7/2001 | WO | WO 03/082129 A2 | 10/2003 | |
| EP | 0947166 B1 | 5/2003 | WO | WO 2004/006789 A1 | 1/2004 | |
| EP | 0836832 B1 | 12/2003 | WO | WO 2004/028613 A2 | 4/2004 | |
| EP | 1402837 A1 | 3/2004 | WO | WO 2004/037123 A1 | 5/2004 | |
| EP | 0744918 B1 | 4/2004 | WO | WO 2004/052221 A1 | 6/2004 | |
| EP | 0931515 B1 | 8/2004 | WO | WO 2004/086984 A1 | 10/2004 | |
| EP | 1411843 B1 | 10/2004 | WO | WO 2005/009211 A2 | 2/2005 | |
| EP | 1150614 B1 | 11/2004 | WO | WO 2005/018467 A2 | 3/2005 | |
| EP | 1477104 A1 | 11/2004 | WO | WO 2005/037088 A2 | 4/2005 | |
| EP | 1481642 A1 | 12/2004 | WO | WO 2005/048827 A1 | 6/2005 | |
| EP | 1493391 A1 | 1/2005 | WO | WO 2005/065284 A2 | 7/2005 | |
| EP | 0848598 B1 | 2/2005 | WO | WO 2005/097019 A2 | 10/2005 | |
| EP | 1281360 | 3/2005 | WO | WO 2005/097234 A2 | 10/2005 | |

| | | | |
|---|---|---|---|
| WO | WO 2005/112810 A2 | 12/2005 |
| WO | WO 2005/120363 A1 | 12/2005 |
| WO | WO 2006/007399 A1 | 1/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/014063 A2 | 2/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2008/005433 A1 | 1/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/101075 A2 | 8/2008 |
| WO | WO 2008/102154 A2 | 8/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2010/088481 A1 | 8/2010 |

OTHER PUBLICATIONS

K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).

K. Sumiyama et al., "Submucosal Endoscopy with Mucosal Flap Safety Valve," Gastrointest Endosc. Apr. 2007, vol. 65(4) pp. 694-695 (Abstract).

K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).

K. Sumiyama et al., "Endoscopic Caps," Tech. Gastrointest. Endosc., vol. 8, pp. 28-32, 2006.

"Z-Offset Technique Used in the Introduction of Trocar During Laparoscopic Surgery," M.S. Hershey NOTES Presentation to EES NOTES Development Team, Sep. 27, 2007.

F.N. Denans, Nouveau Procede Pour La Guerison Des Plaies Des Intestines. Extrait Des Seances De La Societe Royale De Medecine De Marseille, Pendant Le Mois De Dec. 1825, et le Premier Tremestre De 1826, Séance Du Feb. 24, 1826. Recueil De La Societe Royale De Medecin De Marseille. Marseille: Impr. D'Achard, 1826; 1:127-31. (with English translation).

I. Fraser, "An Historical Perspective on Mechanical Aids in Intestinal Anastamosis," Surg. Gynecol. Obstet. (Oct. 1982), vol. 155, pp. 566-574.

M.E. Ryan et al., "Endoscopic Intervention for Biliary Leaks After Laparoscopic Cholecystectomy: A Multicenter Review," Gastrointest. Endosc., vol. 47(3), 1998, pp. 261-266.

C. Cope, "Creation of Compression Gastroenterostomy by Means of the Oral, Percutaneous, or Surgical Introduction of Magnets: Feasibility Study in Swine," J. Vasc Interv Radiol, (1995), vol. 6(4), pp. 539-545.

J.W. Hazey et al., "Natural Orifice Transgastric Endoscopic Peritoneoscopy in Humans: Initial Clinical Trial," Surg Endosc, (Jan. 2008), vol. 22(1), pp. 16-20.

N. Chopita et al., "Endoscopic Gastroenteric Anastamosis Using Magnets," Endoscopy, (2005), vol. 37(4), pp. 313-317.

C. Cope et al., "Long Term Patency of Experimental Magnetic Compression Gastroenteric Anastomoses Achieved with Covered Stents," Gastrointest Endosc, (2001), vol. 53, pp. 780-784.

H. Okajima et al., "Magnet Compression Anastamosis for Bile Duct Stenosis After Duct to Duct Biliary Reconstruction in Living Donor Liver Transplantation," Liver Transplantation (2005), pp. 473-475.

A. Fritscher-Ravens et al., "Transluminal Endosurgery: Single Lumen Access Anastamotic Device for Flexible Endoscopy," Gastrointestinal Endosc, (2003), vol. 58(4), pp. 585-591.

G.A. Hallenbeck, M.D. et al., "An Instrument for Colorectal Anastomosis Without Sutrues," Dis Col Rectum, (1963), vol. 5, pp. 98-101.

T. Hardy, Jr., M.D. et al., "A Biofragmentable Ring for Sutureless Bowel Anastomosis. An Experimental Study," Dis Col Rectum, (1985), vol. 28, pp. 484-490.

P. O'Neill, M.D. et al., "Nonsuture Intestinal Anastomosis," Am J. Surg, (1962), vol. 104, pp. 761-767.

C.P. Swain, M.D. et al., "Anastomosis at Flexible Endoscopy: An Experimental Study of Compression Button Gastrojejunostomy," Gastrointest Endosc, (1991), vol. 37, pp. 628-632.

J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.

USGI® EndoSurgical Operating System—g-Prox® Tissue Grasper/Approximation Device; [online] URL: http://www.usgimedical.com/eos/components-gprox.htm—accessed May 30, 2008 (2 pages).

Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.

Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).

ERCP; Jackson Siegelbaum Gastroenterology; [online] URL: http://www.gicare.com/pated/epdgs20.htm; accessed Feb. 21, 2008 (3 pages).

D.G. Fong et al., "Transcolonic Ventral Wall Hernia Mesh Fixation in a Porcine Model," Endoscopy 2007; 39: 865-869.

B. Rubinsky, Ph.D., "Irreversible Electroporation in Medicine," Technology in Cancer Research and Treatment, vol. 6, No. 4, Aug. 2007, pp. 255-259.

D.B. Nelson, MD et al., "Endoscopic Hemostatic Devices," Gastrointestinal Endoscopy, vol. 54, No. 6, 2001, pp. 833-840.

U.S. Appl. No. 11/744,271, filed May 4, 2007.
U.S. Appl. No. 11/744,279, filed May 4, 2007.
U.S. Appl. No. 11/796,035, filed Apr. 26, 2007.
U.S. Appl. No. 11/894,358, filed Aug. 21, 2007.
U.S. Appl. No. 11/897,676, filed Aug. 31, 2007.
U.S. Appl. No. 11/968,810, filed Jan. 3, 2008.
U.S. Appl. No. 11/981,070, filed Oct. 31, 2007.
U.S. Appl. No. 11/981,078, filed Oct. 31, 2007.
U.S. Appl. No. 11/981,134, filed Oct. 31, 2007.
U.S. Appl. No. 11/986,084, filed Nov. 20, 2007.
U.S. Appl. No. 11/986,420, filed Nov. 21, 2007.
U.S. Appl. No. 11/986,489 filed Nov. 21, 2007.
U.S. Appl. No. 11/998,370, filed Nov. 29, 2007.
U.S. Appl. No. 12/014,417, filed Jan. 5, 2008.
U.S. Appl. No. 12/019,461, filed Jan. 24, 2008.
U.S. Appl. No. 12/045,318, filed Mar. 10, 2008.
U.S. Appl. No. 12/109,673, filed Apr. 25, 2008.
U.S. Appl. No. 12/109,699, filed Apr. 25, 2008.
U.S. Appl. No. 12/115,916, filed May 6, 2008.
U.S. Appl. No. 12/122,031, filed May 16, 2008.
U.S. Appl. No. 12/129,784, filed May 30, 2008.
U.S. Appl. No. 12/129,880, filed May 30, 2008.
U.S. Appl. No. 12/130,010, filed May 30, 2008.
U.S. Appl. No. 12/130,023, filed May 30, 2008.
U.S. Appl. No. 12/130,224, filed May 30, 2008.
U.S. Appl. No. 12/130,652, filed May 30, 2008.
U.S. Appl. No. 12/133,109, filed Jun. 4, 2008.
U.S. Appl. No. 12/133,953, filed Jun. 5, 2008.
U.S. Appl. No. 12/163,255, filed Jun. 27, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.
U.S. Appl. No. 11/762,855, filed Jun. 14, 2007.
U.S. Appl. No. 12/192,372, filed Aug. 15, 2008.
U.S. Appl. No. 12/203,330, filed Sep. 3, 2008.
U.S. Appl. No. 12/197,749, filed Aug. 25, 2008.
U.S. Appl. No. 12/197,653, filed Aug. 25, 2008.
U.S. Appl. No. 12/202,740, filed Sep. 2, 2008.
U.S. Appl. No. 12/203,458, filed Sep. 3, 2008.

U.S. Appl. No. 12/201,812, filed Aug. 29, 2008.
U.S. Appl. No. 12/207,306, filed Sep. 9, 2008.
U.S. Appl. No. 12/243,334, filed Oct. 1, 2008.
U.S. Appl. No. 12/234,425, filed Sep. 19, 2008.
International Preliminary Report on Patentability for PCT/US2008/061269, Nov. 5, 2009 (9 pages).
Zadno et al., "Linear Superelasticity in Cold-Worked NI-TI," Engineering Aspects of Shape Memory Alloys, pp. 414-419 (1990).
U.S. Appl. No. 13/013,131, filed Jan. 25, 2011.
U.S. Appl. No. 13/013,147, filed Jan. 25, 2011.
U.S. Appl. No. 12/900,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.
Michael S. Kavic, M.D.., "Natural Orifice Translumenal Endoscopic Surgery: "NOTES"", JSLS, vol. 10, pp. 133-134 (2006).
Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: A Porcine Model," Gastrointestinal Endoscopy, vol. 59, No. 1, pp. 89-95, 2004.
Ogando, "Prototype Toots That Go With the Flow," Design News, 2 pages, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
CRE™ Pulmonary Balloon Dilator; [online] URL: http://www.bostonscientific.com/Device.bsci?page=HCP_Overview&navRelId=1000.1003&method=D..., accessed Jul. 18, 2008 (4 pages).
J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.
K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).
D. Wilhelm et al., "An Innovative, Safe and Sterile Sigmoid Access (ISSA) for NOTES," Endoscopy 2007, vol. 39, pp. 401-406.
Nakazawa et al., "Radiofrequency Ablation of Hepatocellular Carcinoma: Correlation Between Local Tumor Progression After Ablation and Ablative Margin," AJR, 188, pp. 480-488 (Feb. 2007).
Miklavčič et al., "A validated model of in vivo electric field distribution in tissues for electrochemotherapy and for DNA electrotransfer for gene therapy," Biochimica et Biophysica Acta, 1523, pp. 73-83 (2000).
Evans, "Ablative and catherther-delivered therapies for colorectal liver metastases (CRLM)," EJSO, 33, pp. S64-S75 (2007).
Wong et al., "Combined Percutaneous Radiofrequency Ablation and Ethanol Injection for Hepatocellular Carcinoma in High-Risk Locations," AJR, 190, pp. W187-W195 (2008).

Heller et al., "Electrically mediated plasmid DNA delivery to hepatocellular carcinomas in vivo," Gene Therapy, 7, pp. 826-829 (2000).
Widera et al., "Increased DNA Vaccine Delivery and Immunogenicity by Electroporation in Vivo," The Journal of Immunology, 164, pp. 4635-4640 (2000).
Weaver et al., "Theory of electroporation: A review," Bioelectrochemistry and Bioenergetics, 41, pp. 135-160 (1996).
Mulier et al., "Radiofrequency Ablation Versus Resection for Resectable Colorectal Liver Metastases: Time for a Randomized Trial?" Annals of Surgical Oncology, 15(1), pp. 144-157 (2008).
Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).
Guyton et al., "Membrane Potentials and Action Potentials," W.B. Sanders, ed. Textbook of Medical Physiology, p. 56 (2000).
Guyton et al., "Contraction of Skeletal Muscle," Textbook of Medical Physiology, pp. 82-84 (2000).
"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).
"Ethicon Endo-Surgery Studies Presented At DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).
Castellvi et al., "Hybrid Transvaginal NOTES Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).
Castellvi et al., "Hybrid Transvaginal NOTES Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).
OCTO Port Modular Laparoscopy System for Single Incision Access, Jan. 4, 2010; URL http://www.medgadget.com/archives/2010/01/octo_port_modular_laparo...; accessed Jan. 5, 2010 (4 pages).
Hakko Retractors, obtained Aug. 25, 2009 (5 pages).
U.S. Appl. No. 12/607,252, filed Oct. 28, 2009.
U.S. Appl. No. 12/580,400, filed Oct. 16, 2009.
U.S. Appl. No. 12/607,388, filed Oct. 28, 2009.
U.S. Appl. No. 12/612,911, filed Nov. 5, 2009.
U.S. Appl. No. 12/614,143, filed Nov. 6, 2009.
U.S. Appl. No. 12/617,998, filed Nov. 13, 2009.
U.S. Appl. No. 12/640,440, filed Dec. 17, 2009.
U.S. Appl. No. 12/640,469, filed Dec. 17, 2009.
U.S. Appl. No. 12/640,476, filed Dec. 17, 2009.
U.S. Appl. No. 12/640,492, filed Dec. 17, 2009.
U.S. Appl. No. 12/641,823, filed Dec. 18, 2009.
U.S. Appl. No. 12/641,853, filed Dec. 18, 2009.
U.S. Appl. No. 12/641,837, filed Dec. 18, 2009.
U.S. Appl. No. 12/651,181, filed Dec. 31, 2009.
U.S. Appl. No. 12/696,598, filed Jan. 29, 2010.
U.S. Appl. No. 12/696,626, filed Jan. 29, 2010.
U.S. Appl. No. 12/752,701, filed Apr. 1, 2010.

* cited by examiner

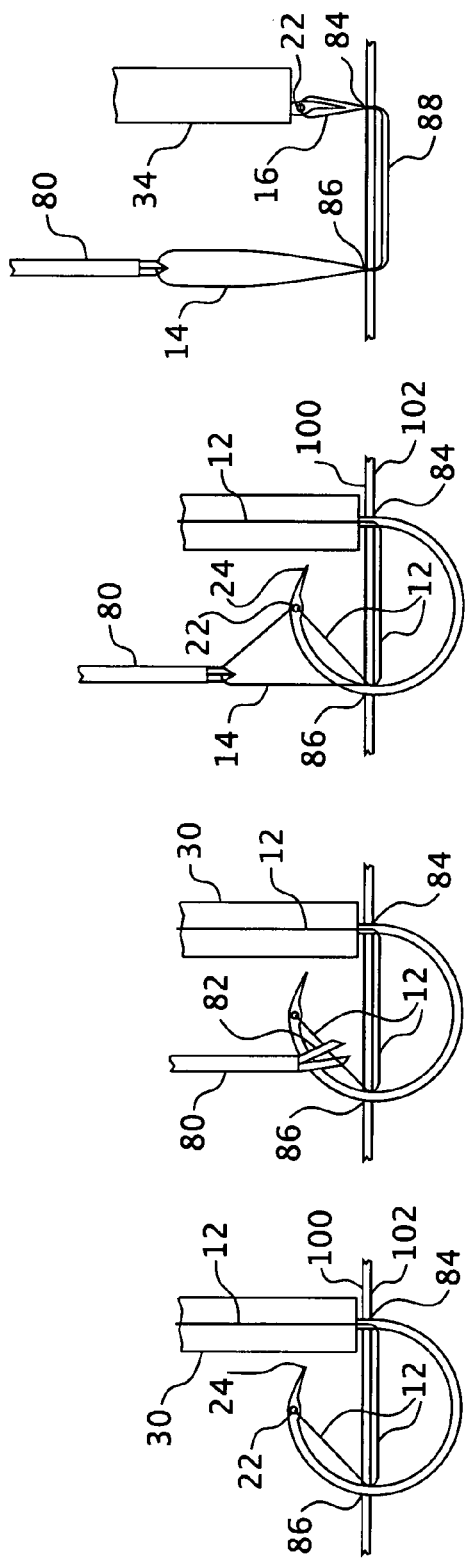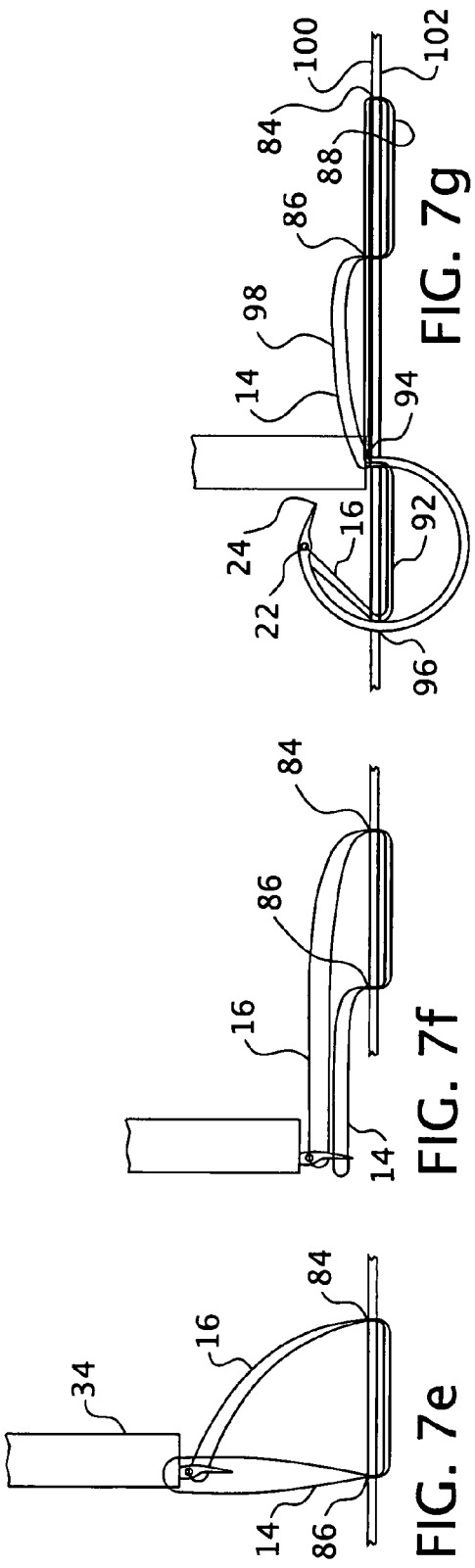

CURVED NEEDLE SUTURING TOOL

FIELD OF THE INVENTION

The present invention relates to tools for surgical suturing, and more particularly, to a curved needle and tool for endoscopic surgical suturing, including, for example, natural orifice transenteric surgery.

BACKGROUND

Sutures are used to approximate, or bring together, tissue separated, for example, by some trauma, or wound or during a surgical procedure to close an incision or an organ perforation. Suturing instruments generally include a needle and a trailing length of suture material. In endoscopic procedures, the instruments placed through an instrument channel may include needles and sutures for stitching such a wound, incision or perforation within the patient's body cavity.

Physicians have often used endoscopes to examine, to biopsy, and to ablate the tissue of patients within lumens such as the esophagus and the bowel or other body cavity and internal patient sites. An endoscope generally includes either a rigid or flexible tube containing one or more optical fiber systems and, for operative uses (human or veterinary), one or more channels for passage of medical instruments. The optical system includes a light delivery system to illuminate the organ or site under inspection and a camera system to transmit the image of the site of interest to the viewer. The light source is normally outside the body and the light is typically directed via optical fiber bundles to the area of interest. The instrument channels and optical fiber bundles open into the body at the distal end of the endoscope and are generally parallel to the axis of the flexible endoscope.

A physician performing a therapeutic procedure with the use of an endoscope places flexible instruments through the instrument channels near the site within the body lumen or cavity where a procedure is to be performed while visualizing and illuminating an internal site using the optical fiber bundles.

More recently, a surgical technique known as natural orifice transenteric surgery (NOTES) is attracting interest. NOTES may be performed with an endoscope that is passed through a natural orifice, such as the patient's mouth, nose or anus, then through an internal incision in the stomach or colon, for example, thus avoiding any external incisions or scars. The NOTES technique has been used for diagnostic and therapeutic procedures in animal models, including transgastric (through the stomach) organ removal. Transcolonic approaches are also advocated for access to upper abdominal structures that may be more difficult to work with using a transgastric approach.

To minimize the trauma experienced by patients, both the number and diameter of the canula inserted into a patient should be minimized. When a procedure requires suturing tissue, a problem arises in the types of needles that can be delivered to the surgical site. Many surgeons prefer to use curved needles which are typically in the range of ¼ to ⅝ of a circle (i.e. an arc whose interior angle is in the range of about 90°-225°). Needles of these dimensions would require canula, or endoscope working channels, large enough to accommodate the arc of the needle, which in many procedures, is not feasible. The preferred curved surgical needles cannot pass through the preferred, narrower, canula to the surgical site.

In an effort to resolve the problem, alloys that display a shape memory effect, such as those having approximately 50 atomic % nickel (Ni) and 50 atomic % titanium (Ti), are now widely used. The shape memory effect is arises due to a phase change that takes place in certain alloys as they are cooled or heated through their characteristic transformation temperature. The best known shape memory alloys are Ni—Ti (Nitinol) alloys in which the phase change is from an ordered cubic crystal form above the transformation temperature to a crystalline phase below the transformation temperature. The transformation is known as a martensitic transformation between a high temperature "austenitic" form and a low temperature "martensitic" form. An alloy becomes martensitic over a narrow temperature range as it is cooled through its transformation temperature and becomes austenitic over a narrow and slightly higher temperature range as it is heated through its transformation temperature. For a given alloy composition in a given annealed condition, the transformation takes place at a predictable, repeatable temperature. The transformation takes place virtually instantaneously when the alloy in one phase reaches a temperature at which the other phase is thermodynamically more stable.

Shape memory alloys have been used for the manufacture of surgical needles wherein a surgical needle is fabricated from a shape memory alloy into the desired "arc" shape. The arc is maintained at a temperature well above the austenitic phase. The needle is then cooled, transforming the material to the martensitic phase. While in the martensitic phase, the needle is deformed (for example, straightened) to the extent necessary to be able to pass through a canula.

U.S. Pat. No. 4,926,860 discloses arthroscopic instrumentation that takes advantage of the "superelasticity" inherent in shape memory alloys. Similar technology is disclosed in U.S. Pat. No. 4,984,581. U.S. Pat. No. 5,597,378 describes a method of making a shape memory alloy canula.

U.S. Pat. No. 5,219,358 discloses a method for introducing a curved needle to a surgical site in a patient and comprises the steps of (a) inserting a canula into the patient to permit access form outside the patient to the surgical site, (b) providing a shape-metal-alloy needle that, having been formed into an arc shape and tempered at an elevated temperature, has been formed into an elongated shape while in a first, low-temperature state, (c) passing the elongated needle through the canula, and (d) heating the needle to a temperature at which the alloy is converted to a second, high-temperature state, thereby causing the needle to return to the arc shape. Heat can be provided, for example, by an illumination light, by a laser, or by a cautery instrument of any type used in endoscopic surgery. The needle is transformed to the austenitic phase and reverts to the curved shape. Thus, the alloy used for shape memory effect surgical needles preferably undergoes its phase transformation in a narrow range near normal body temperature. Since practical and medical reasons limit the temperature to which the needle can be heated at the surgical site, the alloy is preferably austenitic at a temperature slightly below body temperature, for example, at about 35° C. and above, or room temperature, about 25° C.

Advances in shape memory effect materials and the manufacture of curved needles with such materials makes the use of curved needles in endoscopic surgery possible. However, it has been found that in the process of puncturing a patient's tissue at an internal site through a canula or the working channel of an endoscope, there is a tendency for the tissue to shift. This is particularly true for tissues of the gastrointestinal tract. The pressure of the curved needle puncturing the tissue, first in one direction and then in a second opposite direction as the curve of the needle circles around back through the tissue, pulls at the tissue and causes it to shift, ripple or buckle, such that one or both of the first and second punctures of the curved needle are not in the desired location. A means of stabilizing the tissue while suturing with a curved needle is needed.

SUMMARY OF THE INVENTION

A solution to the problems of delivery of a curved needle through a channel and stabilization of the tissue to be sutured is provided by the needle delivery device of the present invention. The needle delivery device includes generally a needle made of a shape memory alloy pre-formed in an unconstrained configuration, such as, for example, an arc or a curved needle. The shape memory alloy may be, for example, a Ni—Ti alloy, such as Nitinol. The needle delivery device also includes a needle delivery guide, a suturing guide and a positioning member. The needle has an eye therein for holding suture material.

The needle delivery guide has a distal end and a proximal end and defines a needle channel for passage of the needle therethrough. The needle channel defines a longitudinal axis and is configured to hold the needle in a constrained configuration, for example, in substantial alignment with the longitudinal axis of the needle channel.

The suturing guide is connected, and preferably pivotally connected, to the delivery guide. The positioning member moves the suturing guide between an extended position and a collapsed position. In various embodiments, when the suturing guide is in the extended position, it may be configured to stabilize the tissue and to guide the needle in its unconstrained configuration. The extended position may also enable access to the suture material by auxiliary instruments.

In one embodiment, the delivery guide may comprise an elongate member and a pair of constraining members that extend axially from the elongate member at its distal end, and together the elongate member and the constraining members define the needle channel. The elongate member is preferably flexible. The constraining members may be rigid for at least a portion of their length. The suturing guide in this embodiment may form a plate that is pivotally attached at a first end to one member of the pair of constraining members, and pivotally attached at an opposing second end to the positioning member. The plate may define an opening for receiving the needle in the unconstrained configuration thereof and further, an access opening for access to the suture material.

In an embodiment of the positioning member, a rod having a distal end and a proximal end is pivotally connected at the distal end to the second end of the plate and slidably connected at the proximal end to the elongate member. The positioning member may further include an elongate rail positioned along a portion of the length of the elongate channel member and a bracket pivotally connected to the proximal end of the rod for sliding engagement with the rail to move the plate between the collapsed position in which the bracket slides proximally along the rail to pivot the plate toward the elongate member and the extended position in which the bracket slides distally along the rail to move the plate away from the elongate member. The extended position of the plate is preferably transverse to the longitudinal axis of the constraining members.

In one embodiment of the present invention, the needle delivery device is intended for use with an endoscope. The elongate member of the needle delivery guide is therefore configured for passage through a first working channel of an endoscope. A grasper is provided for passage through a second working channel of the endoscope for grasping the suture material.

The needle delivery device may also include a means positioned at the proximal end of the needle delivery guide and operatively connected to the positioning member, for effecting the movement of the suturing guide. Alternatively, the positioning member may be pulled proximally and pushed distally by manipulation, by the surgeon, of an instrument, such as a probe or another grasper, inserted into the first working channel with the delivery device.

A method of suturing using the needle delivery device and a method of preparing the needle delivery device are also described.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIGS. 7a-7g schematically illustrate the curved needle assembly and a grasper forming a chain stitch.

DETAILED DESCRIPTION

Figure 1:
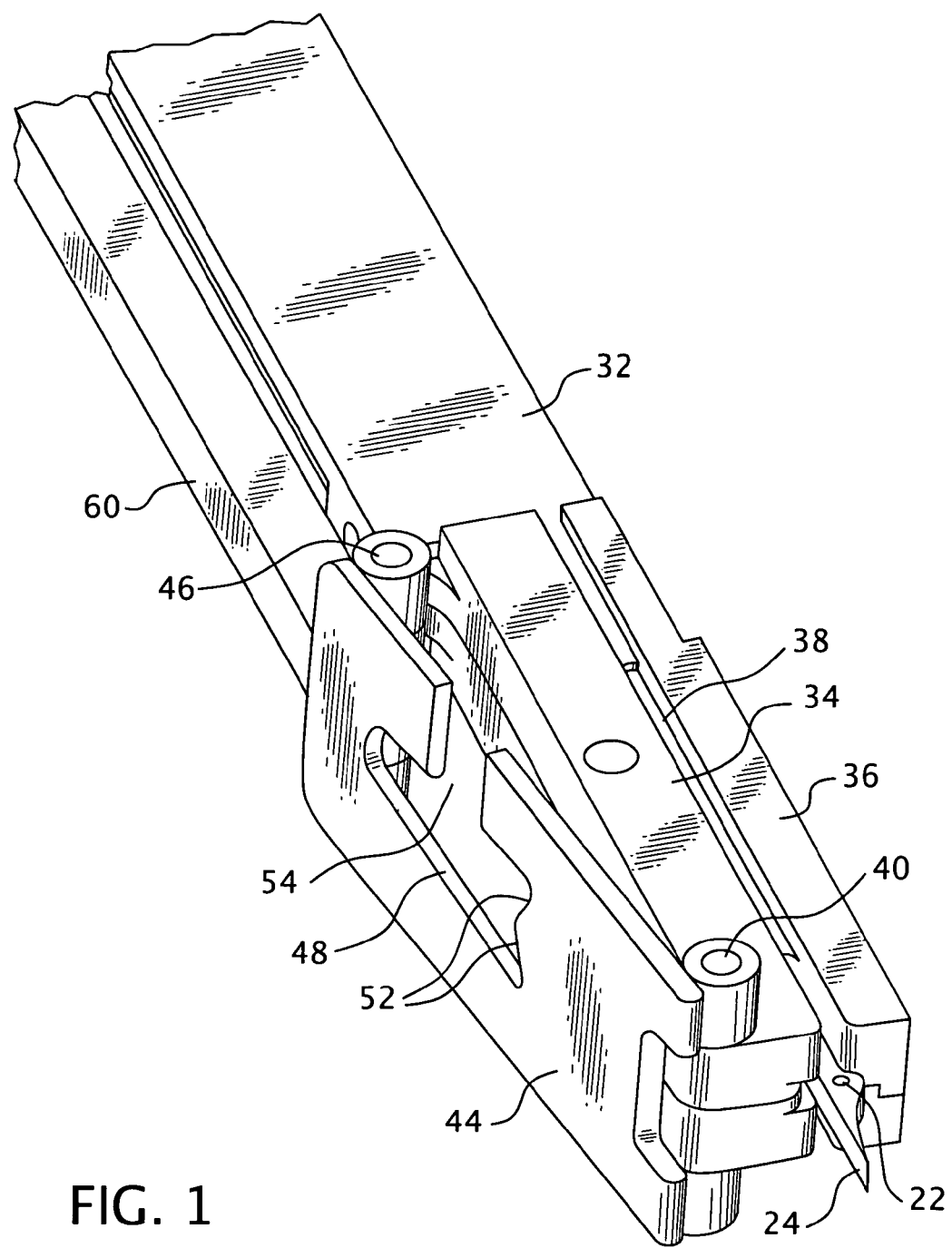
FIG. 1 is a perspective view of an embodiment of the needle delivery device of the present invention with the needle in a compressed state.

Before the present embodiments of an instrument and method for its use are described, it is to be understood that this invention is not limited to the particular process steps and materials disclosed herein as such process steps and materials may vary somewhat. It is also to be understood that the terminology used herein is used for the purpose of describing particular embodiments only and is not intended to be limiting since the scope of the present invention will be limited only by the appended claims.

Unless defined otherwise, all technical and scientific terms used herein have the same meaning as commonly understood to one of ordinary skill in the art to which this invention belongs. Although any method, instrument and materials similar or equivalent to those described herein may be used in the practice or testing of the invention, particular embodiments of a method, instrument and materials are now described.

It must be noted that, as used in this specification and the appended claims, the singular forms "a," "an," and "the" include plural referents unless the content clearly dictates otherwise.

In describing and claiming the present invention, the following terminology will be used in accordance with the definitions set out below.

As used herein, the term "patient," used herein, refers to any human or animal on which a procedure requiring suturing may be performed.

As used herein, the term "biocompatible" includes any material that is compatible with the living tissues and system (s) of a patient by not being substantially toxic or injurious and not causing immunological rejection.

As used herein, the term "bioabsorbable" includes the ability of a material to be dissolved and/or degraded, and absorbed, by the body.

As used herein, the term "shape memory" includes the tendency of a material, such as but not limited to a suitably prepared nickel-titanium alloy ("Nitinol"), to return to a preformed shape, following deformation from such preformed shape.

As used herein, the term "arc" is meant to refer generally to a curved shape. Although an arc of a circle is the shape most commonly used for a surgical needle, "arc" as used herein is not limited to the curve or arc of a circle.

As used herein, the term "integral" means that two or more parts so described are affixed, fastened or joined together so as to move or function together as a substantially unitary part. "Integral" includes, but is not limited to, parts that are continuous in the sense that they are formed from the same continuous material, but also includes discontinuous parts that are joined, fastened or affixed together by any means so as to become substantially immovably affixed to, and substantially unitary with, each other.

As used herein, the term "proximal" (or any form thereof), with respect to a component of an instrument, means that portion of the component that is generally nearest the practitioner, physician, or surgeon, or nearest to the end of the instrument handled by the practitioner, physician, or surgeon, when in use; and with respect to a direction of travel of a component of an instrument, means toward the end of the instrument generally nearest the practitioner, physician, or surgeon, or handled by the practitioner, physician, or surgeon, when in use.

As used herein, the term "distal" (or any form thereof), with respect to a component of an instrument, means that portion of the component that is generally farthest from the practitioner, physician, or surgeon, or farthest from the end of the instrument handled by the practitioner, physician, or surgeon, when in use; and with respect to a direction of travel of a component of an instrument, means away from the end of the instrument generally nearest the practitioner, physician, or surgeon, or handled by the practitioner, physician, or surgeon, when in use.

As used herein, the term "transverse" (or any form thereof), with respect to an axis, means extending in a line, plane or direction that is across such axis, i.e., not co-linear or parallel therewith. "Transverse" as used herein is not to be limited to "perpendicular".

As used herein, the term "longitudinal axis", with respect to an instrument, means the exact or approximate central axis defined by said instrument along its greater dimension, i.e., along its length, from its distal end to its proximal end, and vice versa, and is not intended to be limited to imply a straight line, wherein, for example, an instrument is flexible and includes or may include a bend angle it is intended that "longitudinal axis" as used herein follows such bend angle.

As used herein, the term "internal site" of a patient means a lumen, body cavity or other location in a patient's body including, without limitation, sites accessible through natural orifices or through incisions.

The present invention has application in conventional endoscopic and open surgical instrumentation, as well as application in robotic-assisted surgery. The embodiments shown illustrate the use of the invention in connection with an endoscope within an internal site of a patient. The invention is useful in a variety of minimally invasive medical procedures, including without limitation medical procedures performed through laparoscopic incisions for access to body cavities and internal organs of the body or through natural orifices. The invention also encompasses apparatus and methods employing endoscopic devices in general, including various forms and variations of endoscopes, including without limitation: laparoscopes, gastroscopes, peritoneoscopes, sigmoidoscopes, fiberoptic endoscopes, arthroscopes, amnioscopes, and the like.

One embodiment of the needle delivery device 10 of the present invention is shown in FIGS. 1-6. The device 10 includes generally a needle 20 having a tip 24 for piercing, or puncturing tissue, and an eye 22 for holding a length of suture material 12. Any suitable known suture material may be used and will be determined in most instances by the nature of the procedure and type of tissue to be sutured, as well as the preferences of the surgeon or practitioner performing the procedure.

The preferred material for the needle 20 is a superelastic, shape memory alloy such as Nitinol (Ni—Ti); however, other non Ni—Ti alloys may be used. Any Nitinol alloy selected will have properties whereby the temperature at which the martensitic to austenitic phase change occurs is lower than the working temperature of the device (i.e., room or body temperature). A permanent bend may be heat set in a superelastic Nitinol needle by maintaining the needle in the desired final shape while subjecting it to a prescribed high temperature for a specific time period. The needle can be elastically manipulated far beyond the point at which stainless steel or other metals would experience plastic deformation. Nitinol and other superelastic materials, when sufficiently deformed, undergo a local phase change at the point of stress to what is called "stress-induced martensite". When the stress is released, the material resiliently returns to the austenitic state.

A second method of imparting a permanent bend to the material is by a process commonly known as cold working. Cold working involves mechanically overstressing or over bending the superelastic instrument. The material within the bending region undergoes a localized phase shift from austenite to martensite and does not fully return to its original shape. In the case of the cold-worked instrument, the result is a permanent curve about the bending zone which has been locked in to at least a partial martensitic crystalline state. In contrast, the entire heat-annealed instrument is in an austenitic condition, even in the curved region, and only is temporarily transformed to martensite under sufficient bending stresses. Therefore, the flexural properties of the annealed instrument vary little across its length. Conversely, the bend of a cold-worked instrument, which contains martensite, has increased resistance to deformation and therefore, holds its shape better than the more flexible bend of the pure austenitic instrument. This increased rigidity can be an advantage for certain clinical applications.

Cold working permanently locks a portion of crystalline structure of the bending zone into at least a partial martensitic condition while the unstressed portions of the canula remains in the austenitic state. Cold worked Ni—Ti alloys are discussed in "Linear Superelasticity in Cold-Worked Ni—Ti", (Zadno and Duerig) pp. 414 to 419, in Engineering Aspects of Shape Memory Alloys, Butterworth-Heineman, Boston, Mass. (Duerig et al, editors) which is incorporated herein by reference. In addition to Nitinol, superelastic biocompatible polymeric materials with sufficient rigidity for both deployment and shape memory to assume a desired curve may also be used in certain applications, either alone or in combination with reinforcing metal components.

The primary purpose of using a Nitinol or other superelastic alloys for the needle is that it can be constrained into one shape during its passage to the treatment site, and then deployed into its preformed unconstrained configuration without experiencing any plastic deformation. In the embodiment of the needle 20 shown in the Figures, the preformed configuration is an arc or curve. When not constrained by some deforming pressure, and when heated to its austenitic temperature, the needle 20 assumes its unconstrained, preformed configuration, for example, the arc shape shown. For convenience in this specification and the appended claims, we refer to the curved needle as being in the shape of an arc, although clearly the needle could have any "remembered" shape desired.

Figure 2:
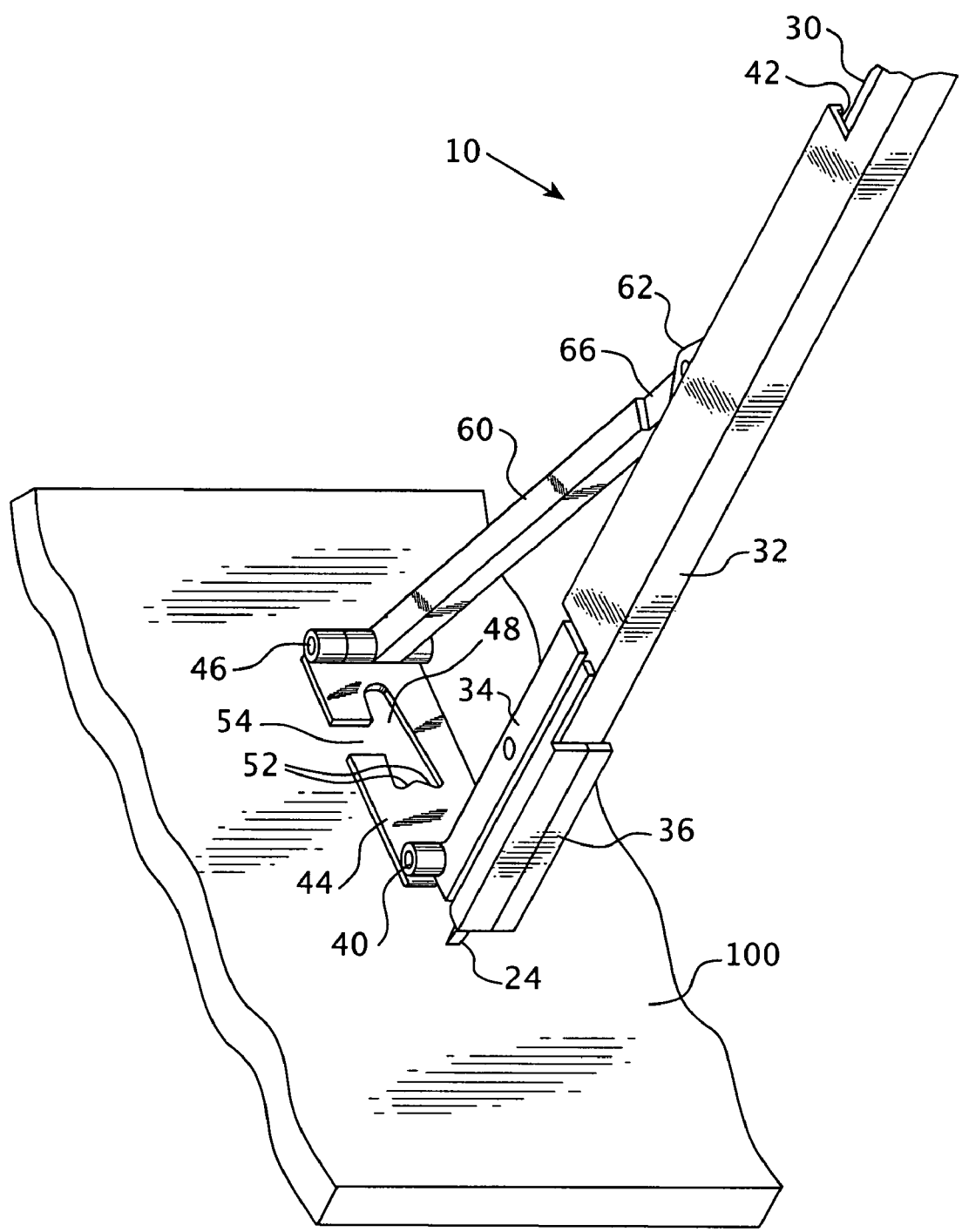
FIG. 2 is a view of the deployment of the suturing guide of the needle delivery device prior to penetration of the tissue.

In the embodiment shown, the needle 20 is constrained when it travels through the needle delivery channel 38 in the delivery guide 32. As shown in FIGS. 1 and 2, the constrained configuration would be linear, or in general alignment with the longitudinal axis of the needle channel 38 in which the needle 20 resides as it is inserted into an endoscope or canula (not shown) for transport to an internal patient site.

In one embodiment, the needle delivery device 10 generally includes, in addition to the needle 20, a delivery guide 32, a suturing guide, which is shown in the form of a plate 44, a positioning member, which is shown as a bar 60 pivotally attached to plate 44 and to the distal end of the delivery guide 32.

Figure 3:
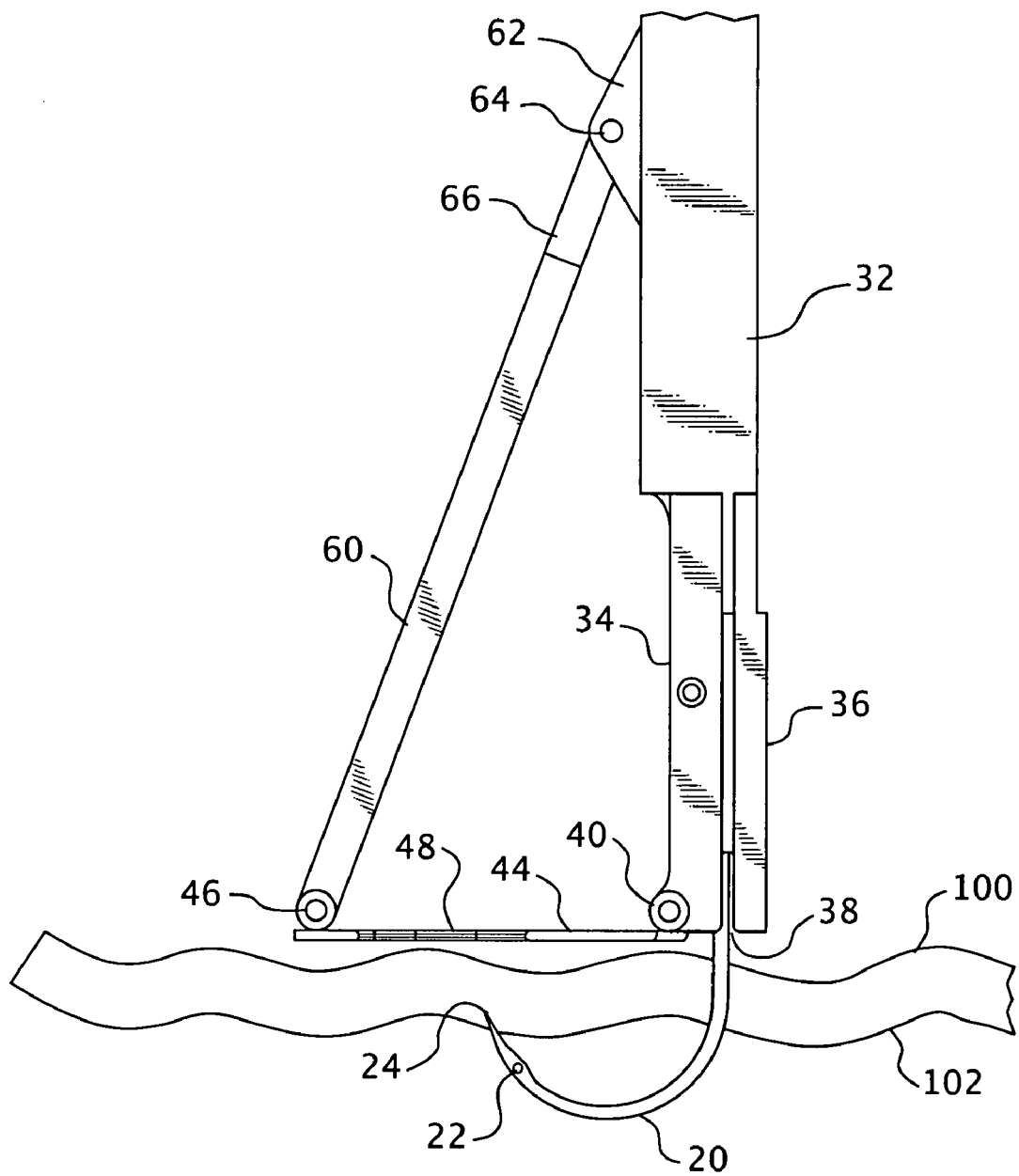
FIG. 3 is a side view illustrating the curved needle having exited the delivery guide and punctured the tissue in a distal direction and beginning the reverse puncture in a proximal direction.

Referring to FIGS. 2 and 3, the delivery guide 32 includes an elongate member 30 and a pair of constraining members 34, 36 defining a needle channel 38 between the front 34 and back 36 constraining members and through the elongate member 30.

The suturing guide includes plate 44 having an opening 48 for passage of the needle 20, as described in more detail hereinafter. Opening 48 has a pair of indentations 52 to define a guide path for each strand of a double stranded suture 12 as the needle 20, in its unconstrained, arced configuration, passes through the tissue from the distal side 102 to the proximal side 100, through opening 48. Plate 44 also includes a cut away section through the side of plate 44 to opening 48 to define an access path 54 through which graspers 80, as illustrated schematically in FIG. 7, can access and grasp a section of suture 12.

Plate 44 is pivotally connected to the front constraining member 34 by pivot pin 40. At the opposite side of plate 44, pivot pins 46 pivotally connect plate 44 to the distal end of a positioning bar 60. Positioning bar 60 includes an area 66 having a reduced width at its proximal end. The proximal end of positioning bar 60 may be pivotally connected to the delivery guide 32 by pivot pins 64 in bracket 62. Positioning bar 60 may have an elongate slot (not shown) for sliding engagement with the pin 64 to allow the proximal end of bar 60 to slide proximally along the side of delivery guide 32 to collapse plate 44 against the delivery guide 32 for travel through the channel of an endoscope or canula and to slide distally and outwardly from delivery guide 32 to extend plate 44 onto the tissue 100.

In an alternative embodiment, as shown in FIG. 2, delivery guide 32 may have a rail 42. The proximal end of positioning bar 60 includes a pin, clevis member or the like for sliding engagement with the rail 42 to allow positioning bar 60 to travel distally to extend plate 44 and proximally to collapse plate 44 against delivery guide 32. In the extended position, the longitudinal axis of plate 44 is transverse, and generally perpendicular to the longitudinal axis of the delivery guide 32.

In use, the needle delivery device 10 would be inserted through the proximal end of a canula or the working channel of an endoscope and directed distally through the canula or channel to the internal patient site in need of suturing. When inserted into such a channel, the positioning bar 60 and plate 44 would be collapsed against the side of the delivery guide 32. Needle 20 would be constrained in the needle channel 38 between constraining members 32 and 34, as shown in FIG. 1.

When the needle delivery device 10 reaches the area within the patient site in need of suturing, as determined by the surgeon or practitioner, the distal tip 24 of the needle 20 is placed against the proximal side 100 of the tissue at the site 84 desired for the first puncture of the needle 20 through the tissue. The positioning bar 60 slides down the rail 42 along the side of the elongate member 32 and pivots at each end about pivot pins 64 and 46 to lower plate 44 from the collapsed position into its extended position, as shown in FIG. 3. Plate 44 pivots about pivot pin 40 away from constraining member 34 to lie across a section of tissue 100 in the intended path of the curved needle 20. When plate 44 is in the extended position, it presses gently against the tissue and holds, or stabilizes, the tissue in position. The needle 20 is deployed from needle channel 38, whereupon, it assumes its unconstrained, preformed configuration, such as the arced shape shown.

Figure 4:
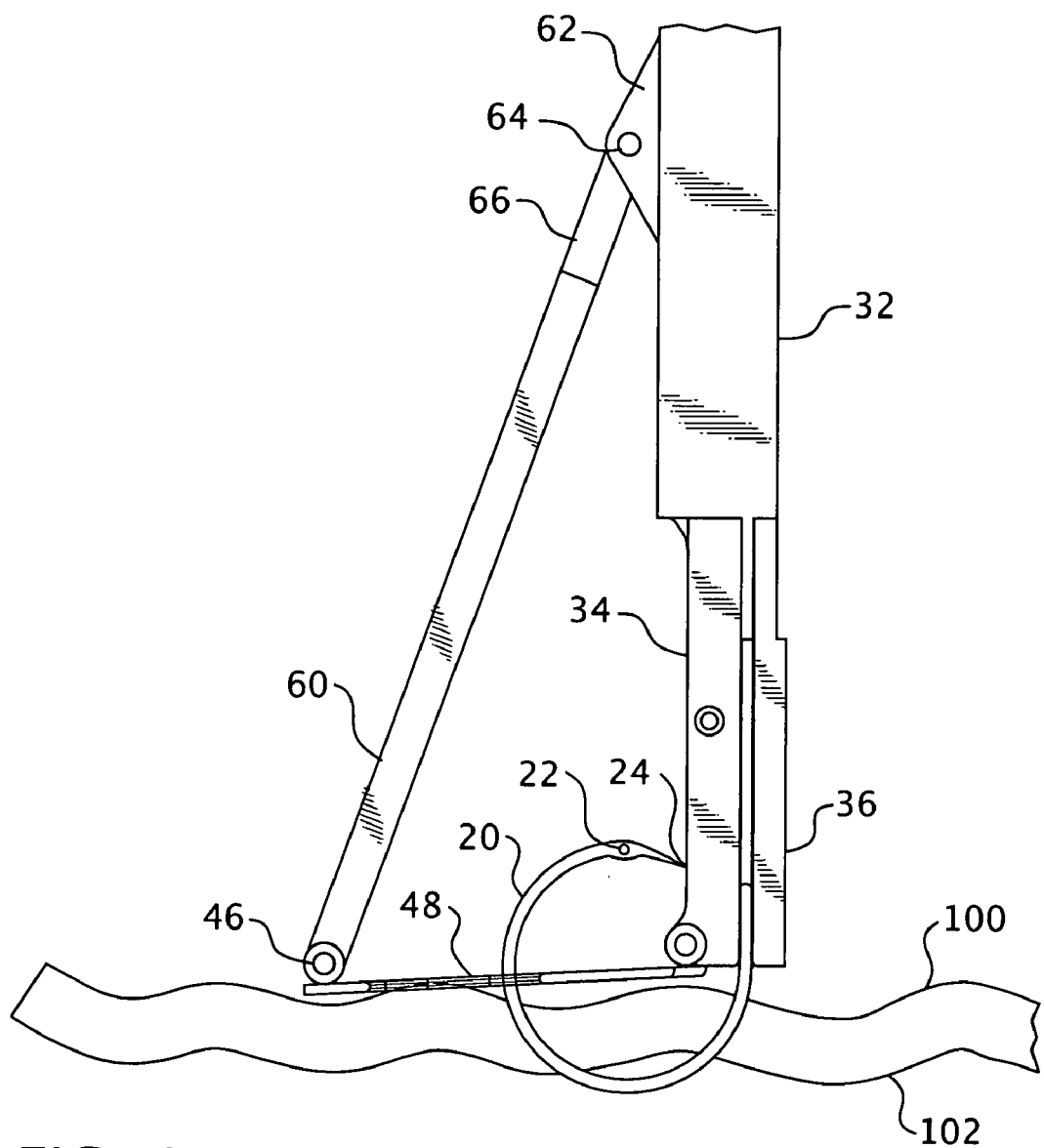
FIG. 4 is a side view illustrating the curved needle after completion of the reverse puncture of the tissue in the proximal direction.
Figure 5:
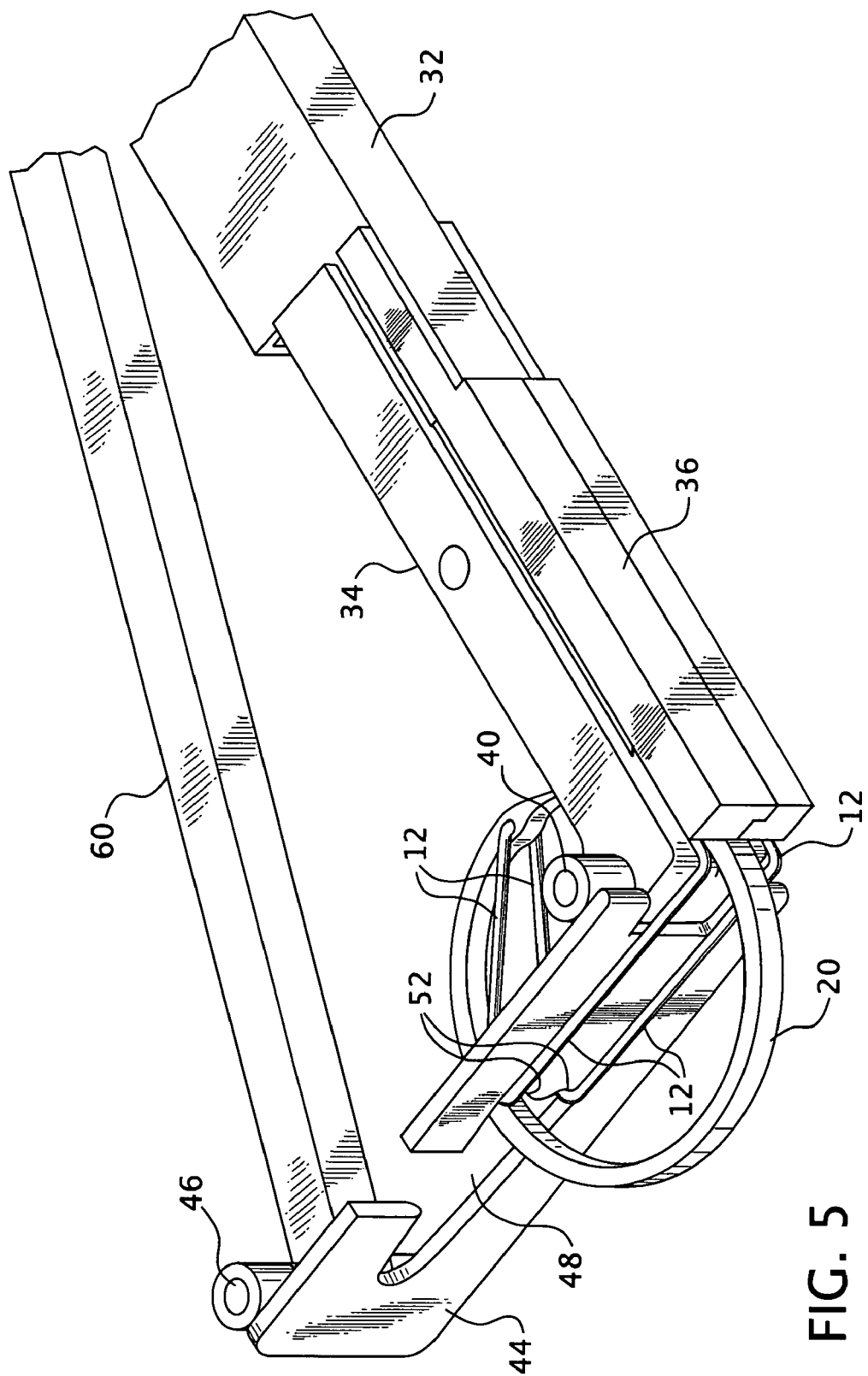
FIG. 5 is an alternative view of the curved needle of FIG. 4 showing the position of the suture after a single stitch.

The tip 24 of needle 20 punctures the proximal side 100 of the patient's tissue at a first puncture site 84 and passes through the tissue to the distal side 102, and curves around to puncture the distal side 102 of the tissue at a second puncture site 86, going back through the tissue in a proximal direction to the proximal side 100, as shown in FIG. 4. Having plate 44 in the extended position on the proximal side 100 of the tissue holds the tissue in position so that the tissue doesn't buckle or ripple and the second puncture 86 occurs at the intended site. The curved needle 20 passes through opening 48 in plate 44, as shown in FIG. 5, pulling the suture material 12, which is attached through the eye 22 of needle 20, through the first and second puncture sites 84, 86. The suture material 12 is guided and separated by the indented sections 52 of opening 48.

The needle 20 is withdrawn back into needle channel 38, back through the second and then the first puncture sites 84, 86. As the needle 20 is pulled into channel 38, it is deformed into the constrained configuration.

Referring to FIG. 7, a suturing procedure is shown schematically that makes advantageous use of the needle delivery device 10 of the present invention. As described above, the needle 20 is directed through a first working channel of an endoscope (not shown) in the distal direction to an internal patient site having tissue in need of suturing and positioned on and passes through the tissue at the desired first puncture site 84. Continued advancement of the portion of needle 20 that remains in the needle channel 38 in the distal direction, causes the tip and trailing arc of the unconstrained curve of the needle 20 to move back through the tissue in the proximal direction, through second puncture site 86, as shown in FIG. 7a. The suture is shown passing through the first and second puncture sites 84, 86. Although not shown in detail in the schematic of FIG. 7, the plate 44 will be in its extended position, on tissue 100 to stabilize the tissue against buckling or rippling or movement away from the path of the needle 20.

As shown in FIG. 7b, a grasper 80 or similar tool that can grasp and hold the suture 12, without damaging it, would be passed through a second working channel of an endoscope (not shown) or through another canula to the internal patient site. The jaws 82 of grasper 80 grasp the suture 12 at a location proximal to the second puncture site 86, preferably between the second puncture site 86 and the eye 22 of needle 20. Referring to FIG. 7c, the grasper 80 pulls the suture 12 proximally, away from the needle 20 to begin the creation of a loop 14 of suture 12. The needle 20 and a retained section of suture 16 are drawn proximally back into the needle channel 38 while the grasper 80 holds the now completely formed suture loop 14. As the needle 20 is drawn back, as shown in FIG. 7d, the curved needle 20 withdraws distally through the second puncture site 86 and through the first puncture site 84 to the needle channel 38. The grasped loop 14 remains on the proximal side 100 of the tissue.

Figure 6:
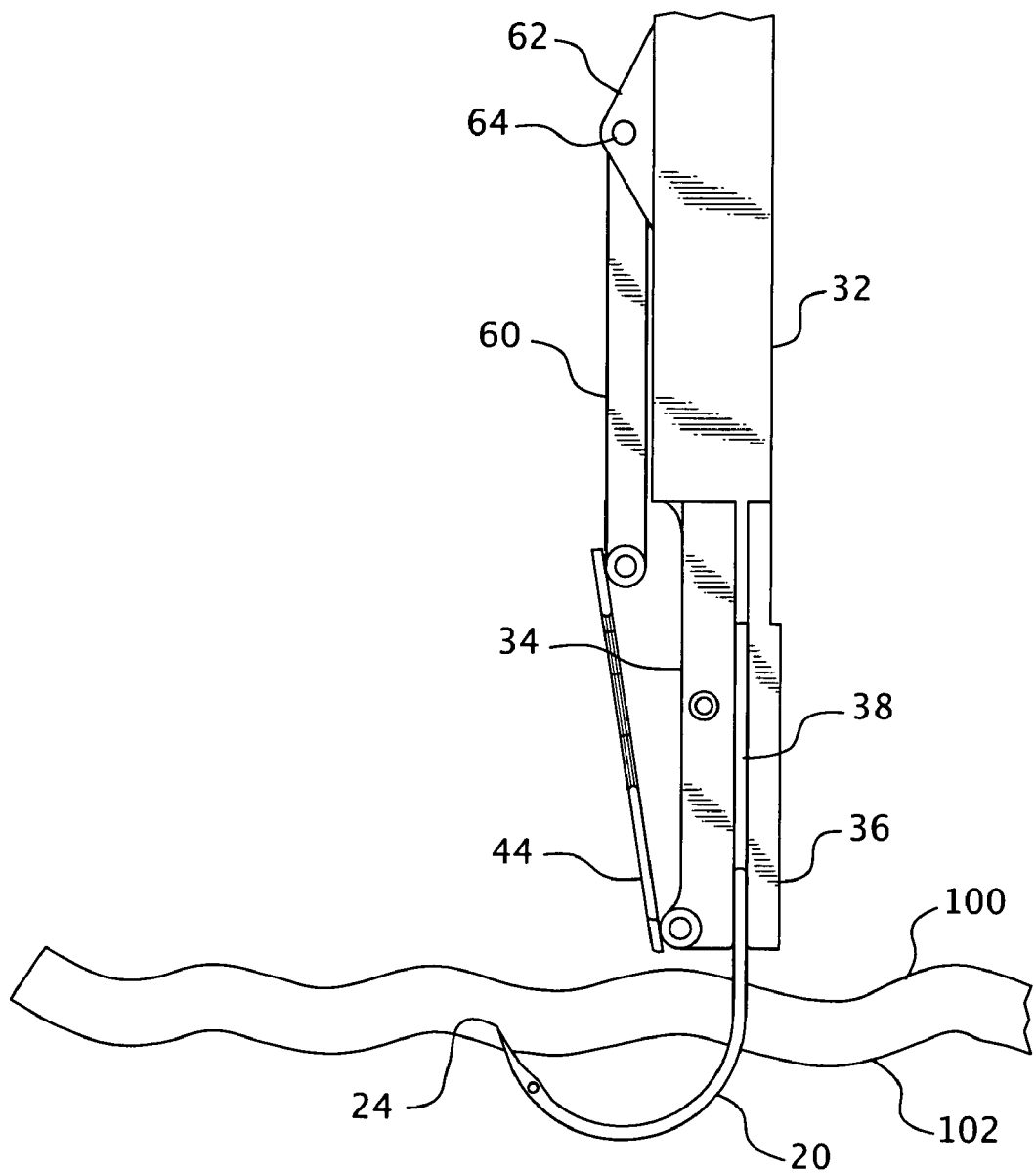
FIG. 6 is a side view of the curved needle being drawn back into the needle delivery device.

At this stage, the surgeon or practitioner, at his or her option, can either (i) complete a single suture stitch 88 by tying the suture material of loop 14 held by the grasper 80, then cutting the tied suture material 12, and moving the plate 44 into the collapsed position, as shown in FIG. 6 for a second single stitch (and any number of additional stitches deemed necessary or desirable by the surgeon or practitioner), or, as shown in FIGS. 7e and 7f, (ii) continue the first stitch by moving the plate 44 of the needle delivery device 10 laterally and passing the tip 24 of needle 20 and the retained suture material 16 through the loop 14 of the suture material 12 held by the grasper 80 and on to the proximal side 100 of the tissue at a third puncture site 94.

The needle 20 is advanced distally out of the needle channel 20 to make the third puncture at the third puncture site 94 and form the second stitch 98. As the needle 20 advances, it assumes the unconstrained, arc configuration and the tip 24 and trailing arc of needle 20 curve back in the proximal direction, pulling the retained suture 16 with it to puncture the distal side 102 of the tissue at the fourth puncture site 96, as shown in FIG. 7g, forming a third stitch 92. By passing the retained suture section 16 through the loop 14 held by grasper 80, the second stitch 98 is linked by the continuous length of suture 12 to the first stitch 88, tying it into place. To continue the chain stitch further, the jaws 82 of grasper 80 pull the suture 12 as shown in FIGS. 7b-d and the needle delivery guide 10 is moved laterally to create another puncture and another stitch as shown in FIGS. 7e-g, linking and tying the third and subsequent stitches.

The steps are repeated until a desired area of the tissue at the internal patient site is sutured, either in a series of single stitches or in a continuous stitch, such as the chain stitch just described. When the stitching is complete, the needle 20 is withdrawn into needle channel 38 into its constrained configuration. Positioning bar 60 is pulled proximally, so that plate 44 is moved into its collapsed position against the side of delivery guide 32. The needle delivery device 10 is withdrawn from the patient site, for example proximally through the working channel of the endoscope or canula.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present invention.

Preferably, the various embodiments of the invention described herein will be processed before patient use. First, a new or used instrument, in this case, a needle delivery device is obtained and if necessary, cleaned. The needle delivery device can then be sterilized by any suitable known sterilization technique. This can be done by any number of ways known to those skilled in the art including beta or gamma radiation, ethylene oxide, or steam. In one sterilization technique, the needle delivery device is placed in a closed and sealed container, such as a plastic or TYVEK bag. The container and instruments are then placed in a field of radiation that can penetrate the container, such as gamma radiation, x-rays, or high-energy electrons. The radiation kills bacteria on the instruments and in the container. The sterilized instruments can then be stored in the sterile container. The sealed container keeps the deployment device and anchors sterile until it is opened in the medical facility.

In summary, numerous benefits are apparent which result from employing the concepts of the invention. The foregoing description of one or more embodiments of the invention has been presented for purposes of illustration and description. It is not intended to be exhaustive or to limit the invention to the precise form disclosed. Obvious modifications or variations are possible in light of the above teachings. The embodiments were chosen and described in order to best illustrate the principles of the invention and its practical application to thereby enable one of ordinary skill in the art to best utilize the invention in various embodiments and with various modifications as are suited to the particular use contemplated. It is intended that the scope of the invention be limited only by the claims appended hereto.

The invention claimed is:

1. A needle delivery device comprising:
    a needle for holding suture material and being made of a shape memory alloy preformed in an unconstrained configuration;
    a needle delivery guide having a needle channel for passage of the needle therethrough, a distal end and a proximal end, said needle channel defining a longitudinal axis and being configured to hold the needle in a constrained configuration, wherein the needle channel of the needle delivery guide is defined by an elongate member and a pair of constraining members extending axially from the elongate member at the distal end of the needle delivery guide;
    a suturing guide connected to the needle delivery guide; and,
    a positioning member for moving the suturing guide between an extended position and a collapsed position, wherein, in said extended position the suturing guide is configured to guide the needle in the unconstrained configuration thereof.

2. The needle delivery device recited in claim 1 wherein at least a portion of the pair of constraining members is rigid.

3. The needle delivery device recited in claim 1 wherein the elongate member is flexible.

4. The needle delivery device recited in claim 1 wherein the suturing guide is a plate pivotally attached at a first end to one member of said pair of constraining members, and pivotally attached at an opposing second end to the positioning member, said plate defining an opening for receiving the needle in the unconstrained configuration thereof.

5. The needle delivery device recited in claim 4 wherein the plate further defines an access opening for access to the suture material.

6. The needle delivery device recited in claim 4 wherein the positioning member comprises a rod having a distal end pivotally connected to the second end of the plate and a proximal end slidably connected to the elongate member.

7. The needle delivery device recited in claim 6 wherein the positioning member further comprises an elongate rail positioned along a portion of the length of the elongate member and a bracket pivotally connected to the proximal end of the rod for sliding engagement with the rail to move the plate between the collapsed position in which the bracket slides proximally along the rail to pivot the plate toward the elongate member and the extended position in which the bracket slides distally along the rail to move the plate away from the elongate member.

8. The needle delivery device recited in claim 7 wherein the constraining members have a longitudinal axis and the extended position of the plate is transverse to the longitudinal axis of the constraining members.

9. The needle delivery device recited in claim 1 wherein the elongate member is configured for passage through a first working channel of an endoscope.

10. The needle delivery device recited in claim 9 further comprising means positioned at the proximal end of the needle delivery guide operatively connected to the positioning member for effecting the movement of the suturing guide.

11. The needle delivery device recited in claim 1 wherein, in the extended position, the suturing guide is positioned to lie on tissue, in use, to stabilize the tissue during suturing thereof.

* * * * *